United States Patent
Sharma et al.

(10) Patent No.: US 9,808,637 B2
(45) Date of Patent: Nov. 7, 2017

(54) VENTRICULAR TACHYCARDIA DETECTION ALGORITHM USING ONLY CARDIAC EVENT INTERVALS

(71) Applicant: Medtronic, Inc., Minneapolis, MN (US)

(72) Inventors: Vinod Sharma, Maple Grove, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 10 days.

(21) Appl. No.: 14/823,405

(22) Filed: Aug. 11, 2015

(65) Prior Publication Data
US 2017/0043173 A1   Feb. 16, 2017

(51) Int. Cl.
| A61N 1/36 | (2006.01) |
|---|---|
| A61N 1/39 | (2006.01) |
| A61N 1/375 | (2006.01) |
| A61N 1/362 | (2006.01) |
| A61N 1/365 | (2006.01) |
| A61N 1/372 | (2006.01) |
| A61N 1/05 | (2006.01) |

(52) U.S. Cl.
CPC ......... *A61N 1/3962* (2013.01); *A61N 1/0573* (2013.01); *A61N 1/365* (2013.01); *A61N 1/3621* (2013.01); *A61N 1/36507* (2013.01); *A61N 1/3756* (2013.01); *A61N 1/37205* (2013.01); *A61N 1/3925* (2013.01); *A61N 1/3987* (2013.01)

(58) Field of Classification Search
CPC .. A61N 1/3756; A61N 1/0573; A61N 1/3925; A61N 1/3621; A61N 1/365
See application file for complete search history.

(56) References Cited

U.S. PATENT DOCUMENTS

| 4,384,585 A | 5/1983 | Zipes |
|---|---|---|
| 4,971,058 A | 11/1990 | Pless et al. |
| 5,113,859 A | 5/1992 | Funke |
| 5,205,283 A | 4/1993 | Olson |
| 5,330,508 A | 7/1994 | Gunderson |
| 5,354,316 A | 10/1994 | Keimel |
| 5,462,060 A | 10/1995 | Jacobson et al. |
| 5,507,782 A | 4/1996 | Kieval et al. |
| 5,545,186 A | 8/1996 | Olson et al. |

(Continued)

OTHER PUBLICATIONS (PCT/US2016/045229) PCT Notification of Transmittal of the International Search Report and the Written Opinion of the International Searching Authority, dated Nov. 17, 2016, 14 pages.

(Continued)

*Primary Examiner* — Tammie K Heller

(57) ABSTRACT

An implantable medical device system includes a pacemaker and an extravascular implantable cardioverter defibrillator (ICD). The pacemaker is configured to acquire a cardiac electrical signal, determine RR intervals from the cardiac electrical signal, apply ventricular tachycardia detection criteria solely to the RR intervals, detect ventricular tachycardia (VT) when the detection criteria are met; and deliver anti-tachycardia pacing in response to detecting the VT before the extravascular ICD delivers a shock therapy.

17 Claims, 10 Drawing Sheets

(56) References Cited

U.S. PATENT DOCUMENTS

| | | | |
|---|---|---|---|
| 5,683,432 A | 11/1997 | Goedeke et al. | |
| 5,730,141 A | 3/1998 | Fain et al. | |
| 5,836,975 A * | 11/1998 | DeGroot | A61N 1/056 607/5 |
| 6,317,632 B1 | 11/2001 | Krig et al. | |
| 6,393,316 B1 | 5/2002 | Gillberg et al. | |
| 6,510,343 B2 | 1/2003 | Armstrong et al. | |
| 6,879,856 B2 | 4/2005 | Stadler et al. | |
| 6,920,356 B2 | 7/2005 | Armstrong et al. | |
| 7,031,771 B2 * | 4/2006 | Brown | A61B 5/02405 600/518 |
| 7,113,824 B2 | 9/2006 | Krig et al. | |
| 7,120,485 B2 | 10/2006 | Glass et al. | |
| 7,522,956 B2 | 4/2009 | Krig et al. | |
| 7,702,384 B2 | 4/2010 | Kim et al. | |
| 8,032,217 B2 | 10/2011 | Kim et al. | |
| 8,046,068 B2 | 10/2011 | Krig et al. | |
| 8,160,684 B2 | 4/2012 | Ghanem et al. | |
| 8,301,244 B2 | 10/2012 | Kim et al. | |
| 8,306,619 B2 | 11/2012 | Krig et al. | |
| 8,433,409 B2 * | 4/2013 | Johnson | A61N 1/375 607/36 |
| 8,437,842 B2 | 5/2013 | Zhang et al. | |
| 8,532,785 B1 | 9/2013 | Crutchfield et al. | |
| 8,541,131 B2 * | 9/2013 | Lund | H01M 2/0232 429/161 |
| 8,594,786 B2 | 11/2013 | Ousdigian | |
| 2004/0093037 A1 | 5/2004 | Henry | |
| 2006/0217621 A1 | 9/2006 | Kim et al. | |
| 2010/0274149 A1 | 10/2010 | Li et al. | |
| 2012/0172892 A1 * | 7/2012 | Grubac | A61N 1/3756 606/129 |
| 2013/0035748 A1 | 2/2013 | Bonner et al. | |
| 2014/0214104 A1 | 7/2014 | Greenhut et al. | |
| 2015/0196756 A1 | 7/2015 | Stahmann et al. | |

OTHER PUBLICATIONS

Anderson, et al., "Leadless Pacing System Including Sensing Extension", U.S. Appl. No. 14/694,910, filed Apr. 23, 2015, 39 pages.

* cited by examiner

VENTRICULAR TACHYCARDIA DETECTION ALGORITHM USING ONLY CARDIAC EVENT INTERVALS

TECHNICAL FIELD

The disclosure relates to medical device systems including an implantable pacemaker and methods for detecting ventricular tachycardia and controlling anti-tachycardia pacing (ATP) therapies delivered by the pacemaker.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. Other IMDs may incorporate electrodes and/or other sensors along or within a housing of the IMD that encloses circuitry and electronic components of the IMD.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers, monitor a patient's heart activity and provide therapeutic electrical stimulation to the heart of the patient via electrodes coupled to the pacemaker. The electrical stimulation provided by the IMD may include signals such as pacing pulses to address abnormal cardiac rhythms such as bradycardia, tachycardia and fibrillation.

An IMD may sense signals representative of intrinsic depolarizations of the heart and analyze the sensed signals to identify normal or abnormal rhythms. For example, the IMD may sense R-waves attendant to the depolarization of the ventricles of the heart and detect a ventricular tachyarrhythmia based on an analysis of the R-waves. Upon detection of an abnormal rhythm, the IMD may deliver an appropriate electrical stimulation signal or signals to restore or maintain a more normal rhythm. For example, an IMD may deliver bradycardia pacing, ATP, and/or cardioversion or defibrillation shocks to the heart upon detecting an abnormal rhythm.

SUMMARY

In general, the disclosure is directed to an IMD system including a pacemaker and an implantable cardioverter defibrillator (ICD). The pacemaker of the IMD system operating according to the techniques of the disclosure detects ventricular tachycardia (VT) by applying only RR interval criteria to an acquired cardiac electrical signal and delivers ATP when VT is detected and before the ICD delivers a shock therapy for treating the VT.

In one example, the disclosure provides an intracardiac pacemaker comprising a housing sized to fit within a heart, at least two electrodes disposed on the housing, a sensing module enclosed within the housing and electrically coupled to the at least two electrodes, a pulse generator enclosed within the housing and electrically coupled to the at least two electrodes, and a control module enclosed within the housing and electrically coupled to the sensing module and the pulse generator. The sensing module is configured to sense R-waves from a first cardiac electrical signal received from the at least two electrodes coupled to the sensing module. The pulse generator is configured to generate cardiac pacing pulses for delivery to the heart via the at least two electrodes. The control module is configured to determine RR intervals between consecutive ones of the sensed R-waves, apply RR interval-based ventricular tachycardia (VT) detection criteria solely to the determined RR intervals, detect a monomorphic VT when the VT detection criteria are met and, control the pulse generator to deliver anti-tachycardia pacing in response to detecting the monomorphic VT, wherein applying the detection criteria solely to the determined RR intervals comprises applying at least a non-sinus rhythm criterion, a supraventricular tachycardia rejection criterion, and a threshold number of tachycardia detection intervals to the RR intervals.

In another example, the disclosure provides an implantable medical device system comprising an implantable pacemaker and an implantable cardioverter defibrillator (ICD) system. The implantable pacemaker includes a housing sized to fit within a heart, at least two electrodes disposed on the housing, a pacemaker sensing module enclosed within the housing and electrically coupled to the at least two electrodes, a pulse generator enclosed within the housing and electrically coupled to the at least two electrodes, and a pacemaker control module enclosed within the housing and electrically coupled to the sensing module and the pulse generator. The pacemaker sensing module being configured to obtain R-waves from a first cardiac electrical signal received from the at least two electrodes coupled to the sensing module. The pulse generator being configured to generate cardiac pacing pulses for delivery to the heart via the at least two electrodes. The pacemaker control module being configured to determine RR intervals between consecutive ones of the sensed R-waves, apply RR interval-based ventricular tachycardia detection criteria solely to the determined RR intervals, detect a monomorphic ventricular tachycardia (VT) when the detection criteria are met, and control the pulse generator to deliver anti-tachycardia pacing in response to detecting the monomorphic VT, wherein applying the detection criteria solely to the determined RR intervals comprises applying at least a non-sinus rhythm criterion, a supraventricular tachycardia rejection criterion, and a threshold number of tachycardia detection intervals to the RR intervals.

The implantable cardioverter defibrillator (ICD) system includes at least one extravascular defibrillation lead having a plurality of extravascular electrodes and an ICD coupled to the at least one extravascular defibrillation lead. The ICD comprises an ICD sensing module electrically coupled to at least a portion of the plurality of extravascular electrodes to receive a second cardiac electrical signal, a defibrillation therapy delivery module comprising at least one high voltage capacitor, the defibrillation therapy deliver module being configured to deliver a shock therapy to the patient's heart via at least one of the plurality of extravascular electrodes of the extravascular defibrillation lead, and an ICD control module electrically coupled to the ICD sensing module and the defibrillation therapy delivery module. The ICD control module being configured to analyze the second cardiac electrical signal received by the ICD sensing module, detect the VT in response to the analyzing, and control the therapy delivery module to charge the at least one high voltage capacitor in response to detecting the VT. The threshold number of tachycardia detection intervals determined from the first cardiac electrical signal by the pacemaker is reached before charging of the at least one high voltage capacitor by the ICD ends.

In another example, the disclosure provides a method of detecting monomorphic ventricular tachycardia (VT) with an implantable pacemaker. The method comprises acquiring, with the implantable pacemaker, a cardiac electrical signal, detecting, with the implantable pacemaker, R-waves within the acquired cardiac electrical signal, determining, with the implantable pacemaker, RR intervals between consecutive ones of the detected R-waves, applying, with the implantable pacemaker, RR interval-based ventricular tachycardia detection criteria solely to the determined RR intervals, the RR interval-based ventricular tachycardia detection criteria being set to identify monomorphic VT while rejecting supraventricular tachycardia, polymorphic VT and ventricular fibrillation (VT), detecting, with the implantable pacemaker, monomorphic VT when the detection criteria are met, and delivering, with the implantable pacemaker, anti-tachycardia pacing in response to detecting the monomorphic VT.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, an implantable medical device (IMD) system is disclosed herein that includes a pacemaker configured to detect monomorphic VT and deliver ATP in response to detecting the monomorphic VT. The pacemaker may be configured to be implanted wholly in a patient's heart in some examples and is referred to herein as an intracardiac pacemaker. The pacemaker detects monomorphic VT using an algorithm that relies solely on cardiac event interval analysis, specifically RR interval (RRI) analysis, for detecting fast, monomorphic VT with high specificity and sensitivity.

When the pacemaker is implemented as an intracardiac pacemaker, the miniaturized size limits the processing and power capacity of the pacemaker. The pacemaker may not have processing capacity available for performing higher level computational tachyarrhythmia discrimination techniques such as cardiac electrical signal waveform morphology analyses that require wavelet transform or other higher processing burden discriminators that are known for use in implantable cardioverter defibrillators (ICDs) for detecting and discriminating tachyarrhythmias. The interval-based ventricular tachycardia detection algorithm described herein provides for detection of monomorphic VT with high sensitivity and specificity without the need for high processing burden discriminators.

Monomorphic VT is characterized by QRS complexes having a common morphology arising from a single origin, having a stable re-entrant circuit for depolarization wavefront propagation. Monomorphic forms of VT may often be successfully terminated by ATP. ATP interrupts the electrical pathway of the VT, allowing a normal sinus rhythm to be restored. Polymorphic VT, on the other hand, is characterized by QRS complexes that do not share a common morphology and arise from multiple sites of origin, having complex, unstable circuits for depolarization wavefront propagation. Polymorphic VT and VF are treated with cardioversion/defibrillation (CV/DF) shocks which reset the disorganized electrical activity of the heart by depolarizing all of the cardiac tissue at once and allowing a normal heart rhythm to restart.

ATP pulses delivered by intracardiac electrodes are much smaller in energy and cause little or no patient discomfort compared to high voltage CV/DF shocks delivered by an ICD, which can cause considerable patient discomfort but are life-saving when needed. As described herein a pacemaker and an ICD included in an IMD system may operate cooperatively to treat monomorphic VT with ATP delivered by the pacemaker before resorting to CV/DF shocks delivered by the ICD to restore a normal heart rhythm, thereby minimizing patient discomfort and potentially conserving ICD battery longevity among other things.

Figure 1A:
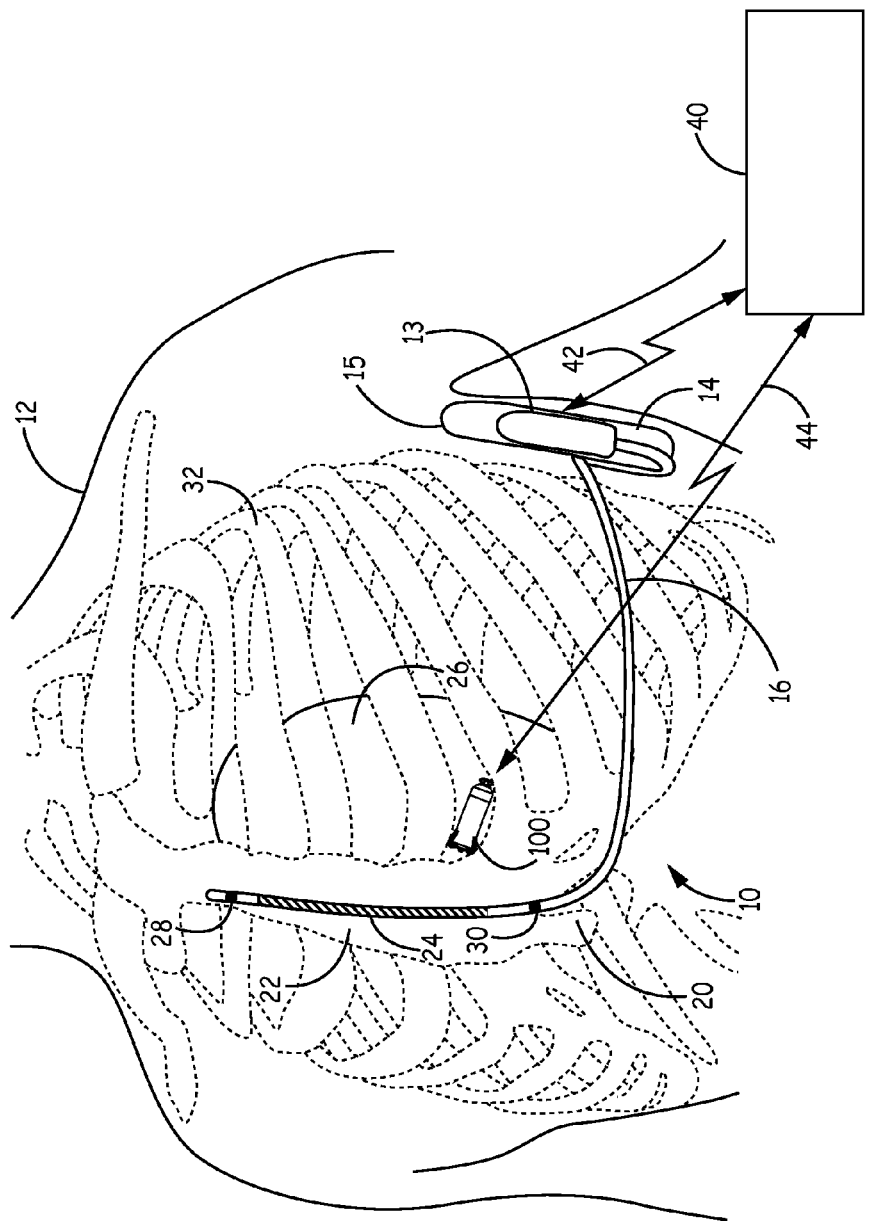
FIG. 1A is a conceptual diagram illustrating an IMD system used to sense cardiac electrical signals in a patient and provide therapies to the patient's heart.

FIG. 1A is a conceptual diagram illustrating an IMD system 10 used to sense cardiac electrical signals in patient 12 and provide therapy to heart 26. IMD system 10 includes an intracardiac pacemaker 100 and ICD 14 coupled to an extravascular defibrillation lead 16. Pacemaker 100 is configured to acquire an intracardiac electrogram (EGM) signal for sensing cardiac events, e.g., R-waves attendant to the depolarization of the ventricles, and determining a need for pacing pulses. Pacemaker 100 may be configured to deliver bradycardia pacing in the absence of sensed cardiac events. Pacemaker 100 is configured to detect monomorphic VT based on cardiac event intervals, in particular based on RRIs, and deliver ATP therapy in response to a VT detection.

Pacemaker 100 is a transcatheter, intracardiac pacemaker adapted for implantation wholly within the patient's heart 26, e.g., wholly within the right ventricle (RV) in the example of FIG. 1A. Pacemaker 100 may be positioned along an endocardial wall of the RV, e.g., near the RV apex, however other locations within or along heart 26 are possible including epicardial locations. In other examples, pacemaker 100 may be positioned in the left ventricle (LV) of heart 26. In each of these examples, pacemaker 100 detects VT by analysis of RRIs determined between sensed R-waves. Pacemaker 100 is configured to receive an EGM signal via one or more electrodes on the outer housing of the pacemaker 100 and produce electrical stimulation pulses, e.g., pacing pulses, delivered to heart 26 via the one or more electrodes on the outer housing of the pacemaker 100.

IMD system 10 may include ICD 14. Pacemaker 100 may be enabled to deliver ATP only when ICD 14 is present in the patient to provide cardioversion/defibrillation (CV/DF) shock therapy if needed. In some examples, pacemaker 100 is configured to detect fast, monomorphic VT with a high sensitivity in order to deliver ATP prior to and/or during high voltage capacitor charging by ICD 14 in preparation for delivering a CV/DF shock by ICD 14 for terminating the VT. ICD 14 is shown implanted subcutaneously on the left side of patient 12 and connected to defibrillation lead 16 via a connector assembly 13. Defibrillation lead 16 is shown extending medially from ICD 14 toward sternum 22 and xiphoid process 20 of patient 12. At a location near xiphoid process 20 defibrillation lead 16 bends or turns and extends subcutaneously superior, substantially parallel to sternum 22. Defibrillation lead 16 may be implanted such that lead 16 extends alongside sternum 22.

Extravascular defibrillation lead 16 includes one or more extravascular electrodes, e.g., located exclusive of the heart (i.e., not on or within the heart 26). In the example illustrated in FIG. 1A, defibrillation lead 16 includes a defibrillation electrode 24, which may be an elongated coil electrode, and a pair of sensing electrodes 28 and 30. Defibrillation lead 16 is placed along sternum 22 such that a therapy vector between defibrillation electrode 24 and the housing 15 of ICD 14 is substantially across one or both ventricles of heart 26. Other ICD implant locations and lead and electrode systems may be used in combination with pacemaker 100. In the example illustrated in FIG. 1, lead 16 is implanted subcutaneously, e.g., such that extravascular electrodes 24, 28, and 30 are located between the skin and the ribs or sternum 22, remaining external to the thoracic cavity. In other examples, lead 16 may be advanced such that extravascular electrodes 24, 28, and 30 are located substernally or within ribcage 32, i.e., intra-thoracically.

Although ICD 14 is illustrated as being implanted near a midaxillary line of patient 12, ICD 14 may also be implanted at other subcutaneous locations on patient 12, such as further posterior on the torso toward the posterior axillary line, further anterior on the torso toward the anterior axillary line, or in a pectoral region, or at other locations of patient 12. In instances in which ICD 14 is implanted pectorally, lead 16 may follow a different path, e.g., across the upper chest area and inferior along sternum 22.

ICD 14 includes a housing 15 that forms a hermetic seal that protects electronic circuitry and other components within ICD 14. The housing 15 may be formed of an electrically conductive metal, e.g., a stainless steel or titanium alloy, to functions as an electrode (sometimes referred to as a housing electrode or "can" electrode) that is used in combination with extravascular electrodes 24, 28 and 30 to deliver a therapy to heart 26 or to sense electrical activity of heart 26.

ICD 14 may sense electrical activity of heart 26 via one or more sensing vectors that include combinations of electrodes 28 and 30 and housing 15. For example, ICD 14 may obtain electrical signals, e.g., ECG signals, using a sensing vector between electrodes 28 and 30, between electrode 28 and housing 15, between electrode 30 and housing 15, or any combination thereof. In some instances, ICD 14 may even sense cardiac electrical signals using a sensing vector that includes defibrillation electrode 24, such as a sensing vector between defibrillation electrode 24 and one of electrodes 28 and 30, or a sensing vector between defibrillation electrode 24 and the housing 15.

ICD 14 and pacemaker 100 are each configured to detect VT from cardiac electrical signals received via respective electrodes coupled to respective sensing modules within each of the ICD 14 and pacemaker 100. ICD 14 and pacemaker 100, however, may not be configured to communicate directly with each other. Pacemaker 100 is configured to detect monomorphic VT with high sensitivity and reject supraventricular tachycardia (SVT) and polymorphic VT/VF with high specificity such that pacemaker 100 is enabled to detect monomorphic VT with high sensitivity and specificity. In this way, pacemaker 100 detects VT when the VT is amenable to ATP termination. When pacemaker 100 detects VT, ATP is delivered by pacemaker 100 prior to any therapy delivered by ICD 14.

ICD 14 analyzes sensed ECG signals to detect VT and VF and in response to detecting VT/VF may generate and deliver one or more defibrillation shocks via a therapy vector that includes defibrillation electrode 24 and the housing 15. It is assumed that ICD 14 will detect a VT episode that is detected by pacemaker 100 at approximately the same time or earlier than the pacemaker 100, for example within 1 to 10 cardiac cycles. ICD 14 begins charging high voltage capacitors for delivering a shock for treating the detected VT. If the VT is terminated by ATP delivered by pacemaker 100 prior to or during ICD capacitor charging, ICD 14 will cancel the scheduled shock therapy. A predetermined shock delay time, e.g., 15 to 20 seconds, between monomorphic VT detection and shock delivery may be set by ICD 14 to allow a predictable number of ATP sequences to be delivered by pacemaker 100 prior to ICD shock delivery in some examples. In other examples, the number of ATP sequences attempted by pacemaker 100 is limited to the number of ATP sequences that can be completed during an expected ICD capacitor charging time. In this way, ICD 14 and pacemaker 100 may operate as a system for detecting monomorphic VT and initially attempting to terminate the VT by ATP before a shock therapy is delivered, potentially precluding the need for the shock.

Pacemaker 100 and ICD 14 may each be capable of bidirectional wireless communication with an external device 40. External device 40 is often referred to as a "programmer" because it is typically used by a physician, technician, nurse, clinician or other qualified user for programming operating parameters in pacemaker 100 and ICD 14. Operating parameters, such as sensing and therapy delivery control parameters, may be programmed into pacemaker 100 and ICD 14 using external device 40. External device 40 may be located in a clinic, hospital or other medical facility. External device 40 may alternatively be embodied as a home monitor or a handheld device that may be used in a medical facility, in the patient's home, or another location. Aspects of external device 40 may generally correspond to the external programming/monitoring unit disclosed in U.S. Pat. No. 5,507,782 (Kieval, et al.), hereby incorporated herein by reference in its entirety.

External device 40 establishes a wireless radio frequency (RF) communication link 42 or 44 with a targeted one of ICD 14 or pacemaker 100, respectively, using a communication protocol that appropriately addresses the targeted ICD 14 or pacemaker 100. An example RF telemetry communication system that may be implemented in system 10 is generally disclosed in U.S. Pat. No. 5,683,432 (Goedeke, et al.), hereby incorporated herein by reference in its entirety. Communication links 42 and 44 may be established between the respective ICD 14 or pacemaker 100 and external device 40 via a radio frequency (RF) link in the Medical Implant Communication Service (MICS) band, Medical Data Service (MEDS) band, BLUETOOTH® wireless technology or Wi-Fi.

External device 40 may be capable of bi-directional communication with ICD 14 or pacemaker 100 over a wide range of distances, e.g., up to approximately 10 meters. In other examples, telemetry communication pacemaker 100 and ICD 14 may require the use of a programming head placed in proximity of the respective pacemaker 100 or ICD 14 to facilitate data transfer. It is contemplated that external device 40 may be in wired or wireless connection to a communications for transferring data to a remote database or computer to allow remote management of the patient 12. As indicated above, ICD 14 and pacemaker 100 may not be configured to communicate directly with each other. In other examples, ICD 14 and pacemaker 100 may be capable of sending and receiving wireless RF communication signals to each other or communicate via tissue conductance communication (TCC). In these cases, pacemaker 100 may transmit a signal to ICD 14 confirming that monomorphic VT has been detected and that ATP is imminent, being delivered, or is complete. Aspects of TCC between two implanted devices are generally disclosed in U.S. Pat. No. 5,113,859 (Funke), incorporated herein by reference in its entirety.

Figure 1B:
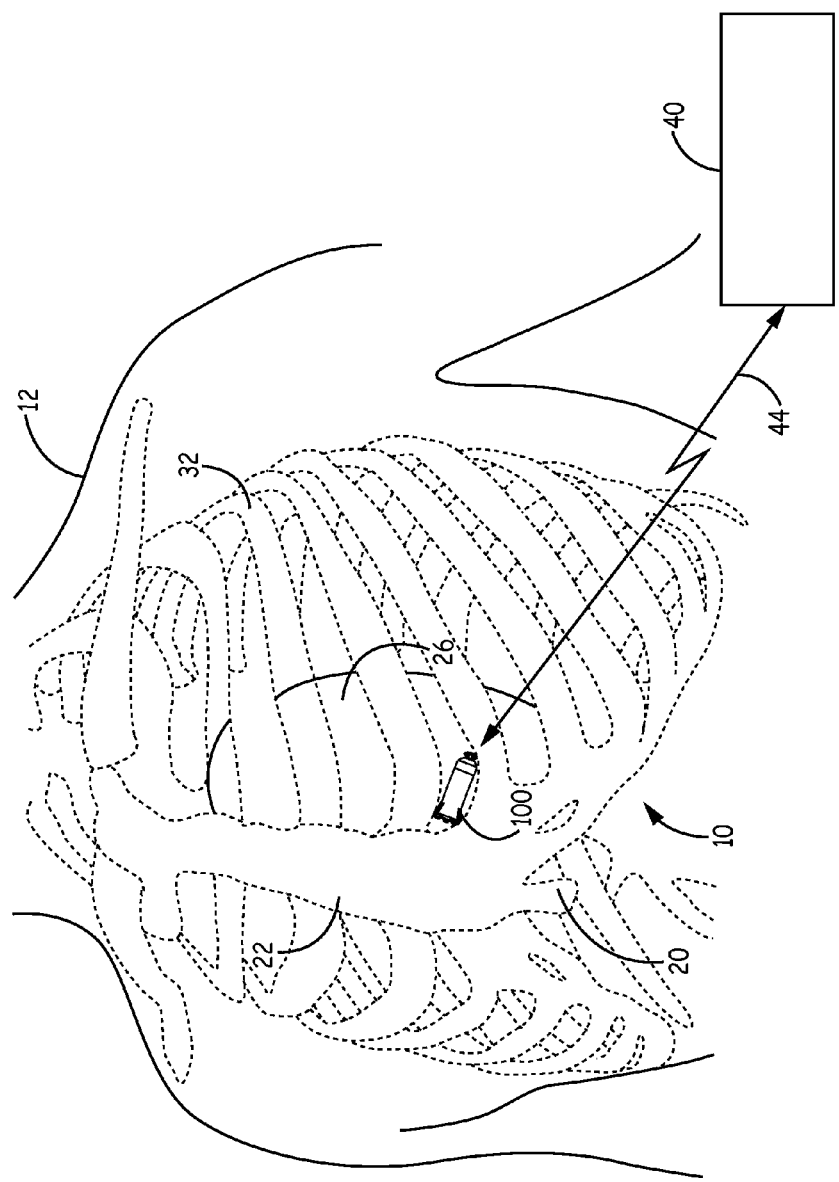
FIG. 1B is a conceptual diagram illustrating an IMD system according to another example.

FIG. 1B is a conceptual diagram of an IMD system 10' according to another example. IM D system 10' includes pacemaker 100, which is configured for bidirectional communication with external device 40 as described above. In some examples, techniques disclosed herein for detecting monomorphic VT and delivering ATP may be implemented in pacemaker 100 without requiring ICD 14 to be included in system 10'. In these examples, one or more ATP sequences may be delivered when monomorphic VT is detected until the VT is terminated.

Figure 2:
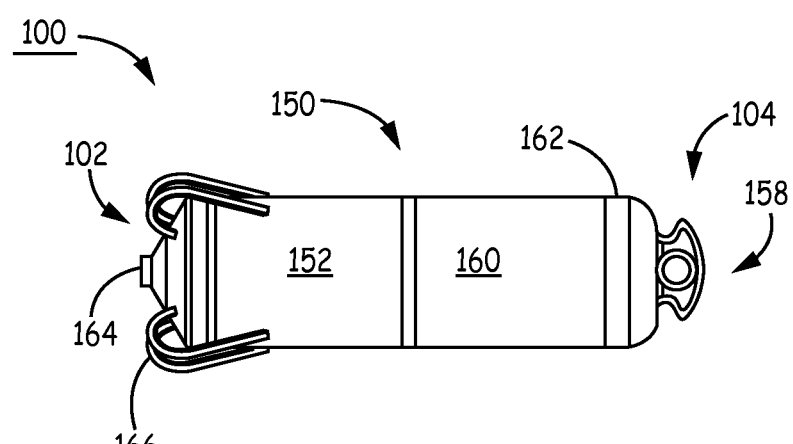
FIG. 2 is a conceptual diagram of the intracardiac pacemaker shown in FIGS. 1A and 1B.

FIG. 2 is a conceptual diagram of pacemaker 100 shown in FIGS. 1A and 1B. Pacemaker 100 may be a transcatheter, intracardiac pacemaker adapted for implantation wholly within the patient's heart 26. To this end, housing 140 of pacemaker 100 may be sized to fit wholly within the patient's heart 26. In one example, housing 150 may have a volume that is less than 1.5 cc and, more preferably, less than 1.0 cc. However, housing 150 may be greater than or equal to 1.5 cc in other examples. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. In alternative embodiments, pacemaker 100 may include two or more ring electrodes, two tip electrodes, and/or other types of electrodes exposed along pacemaker housing 150 for delivering electrical stimulation to heart 26 and for sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others.

Electrodes 162 and 164 may be positioned at locations along pacemaker 100 other than the locations shown or along an insulated conductor extending away from housing 150. For example, one or both of electrodes 162 and/or 164 may be carried by a flexible insulated, electrical conductor extending away from housing 150 at proximal end 104 or distal end 102 for increasing the inter-electrode spacing between electrodes 162 and 164. An intracardiac pacemaker having a flexible electrically conductive extender is generally disclosed in commonly-assigned, pre-grant U.S. Publication No. 2013/0035748 (Bonner, et al.) and in U.S. patent application Ser. No. 14/694,910, filed on Apr. 23, 2015, both of which are incorporated herein by reference in their entirety.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150 may function as an electrode instead of providing a localized electrode such as electrode 162. Electrode 162 may be formed as an uninsulated portion of the housing 150 and serves as an anode return electrode with cathode tip electrode 164, which may be coupled to internal electronic circuitry enclosed by housing 150 via an insulated electrical feedthrough that crosses housing 150.

The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to or against cardiac tissue, e.g., by interacting with the ventricular trabeculae. Fixation tines 166 are configured to anchor pacemaker 100 to position cathode tip electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), hereby incorporated herein by reference in its entirety.

Pacemaker 100 may further include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber. A reduced size of pacemaker 100 enables implantation wholly within a heart chamber in some examples.

Figure 3:
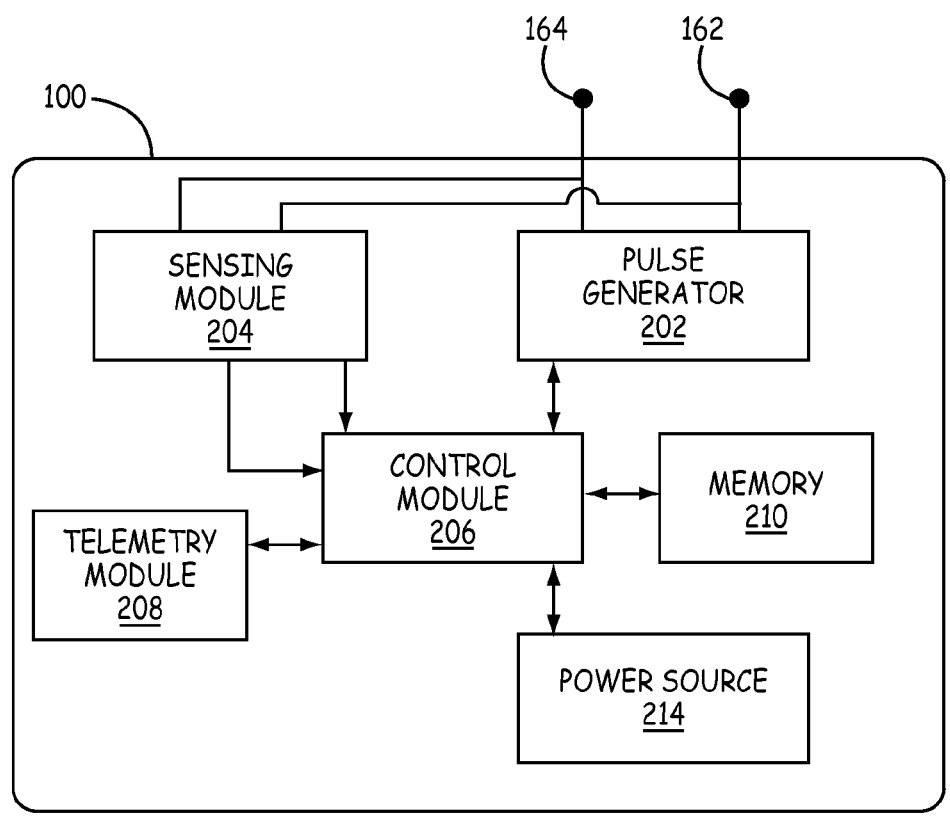
FIG. 3 is a functional block diagram of an example configuration of the pacemaker shown in FIG. 2.

FIG. 3 is a functional block diagram of an example configuration of pacemaker 100 shown in FIG. 2. Pacemaker 100 includes a pulse generator 202, a sensing module 204, a control module 206, telemetry module 208, memory 210, and a power source 214. As used herein, the term "module" refers to an application specific integrated circuit (ASIC), an electronic circuit, a processor (shared, dedicated, or group) that executes one or more software or firmware programs, a combinational logic circuit, a state machine, and/or other suitable components that provide the described functionality. The particular form of software, hardware and/or firmware employed to implement the functionality disclosed herein will be determined primarily by the particular system architecture employed in the IMD system 10 and by the particular detection and therapy delivery methodologies employed by the IMD system 10. Providing software, hardware, and/or firmware to accomplish the described functionality in the context of any modern IMD system, given the disclosure herein, is within the abilities of one of skill in the art.

The functions attributed to pacemaker 100 (or ICD 14) herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate components, or integrated within common hardware, firmware or software components. For example, VT detection and pacing control operations performed by pacemaker 100 may be implemented in control module 206 executing instructions stored in memory 210 and relying on input from sensing module 204.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores timing intervals, counters, or other data used by control module 206 to control the delivery of pacing pulses by pulse generator 202.

Pulse generator 202 generates electrical stimulation pulses that are delivered to heart tissue via electrodes 162 and 164. Electrodes 162 and 164 may be housing-based electrodes as shown in FIG. 2, but one or both electrodes 162 and 164 may alternatively be carried by an insulated, electrical conductor extending away from the pacemaker housing as described above.

Pulse generator 202 may include one or more low voltage capacitors and a charging circuit to charge the capacitor(s) to a programmed pacing pulse voltage. At appropriate times, as controlled by control module 206, the capacitor is coupled to pacing electrodes 162 and 164 to discharge the capacitor voltage and thereby deliver the pacing pulse. Pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 100 for charging a pacing capacitor to a predetermined pacing pulse amplitude and delivering a pacing pulse under the control of control module 206 via cathode tip electrode 164 and anode electrode 162. ATP pulses delivered by pulse generator 202 may be 5 Volts or less.

Control module 206 controls pulse generator 202 to deliver a pacing pulse in response to expiration of a pacing escape interval according to programmed therapy control parameters stored in memory 210. A pace timing and control module included in control module 206 may include an escape interval timer or counter that is set to a pacing escape interval used for controlling the timing of pacing pulses relative to a paced or sensed event. Upon expiration of a pacing escape interval, a pacing pulse is delivered. If a cardiac event is sensed during the pacing escape interval by sensing module 204, the scheduled pacing pulse may be inhibited, and the pacing escape interval may be reset to a new time interval.

In response to detecting a monomorphic VT according to the RRI-based detection criteria described herein, control module 206 controls pulse generator to delivery one or more sequences of ATP pulses according to a programmed therapy regime. ATP sequences may include burst, ramp, burst plus ramp or other ATP pulse patterns. For example, an ATP burst sequence may be delivered including 6 to 10 pacing pulses delivered at pacing pulse intervals that are shorter than up to 97% of the detected RRIs. The amplitude of the ATP pulses may be set to a safety margin above a previously determined pacing capture threshold or at a nominal amplitude, e.g., up to 5 volts, that is expected to capture the ventricles with a high degree of certainty. For example, a typical ATP therapy may be a burst of 8 pulses delivered at 88% of the detected RRI cycle length, with each pulse having an amplitude of 5 volts. If VT is redetected, a second sequence of ATP pulses may be delivered at shorter intervals than the first sequence.

Sensing module 204 receives cardiac EGM signals developed across electrodes 162 and 164. A cardiac event may be sensed by sensing module 204 when the EGM signal crosses a sensing threshold, which may be an auto-adjusting sensing threshold. In response to a sensing threshold crossing, sensing module 204 passes a sensed event signal to control module 206 for use in controlling the timing of pacing pulses. Control module 206 receives R-wave sensed event signals from sensing module 204 and determines RRIs as the intervals occurring between consecutive R-wave sensed event signals. VT detection criteria are applied to the determined RRIs to detect monomorphic VT according to the techniques described below in conjunction with the flow chart of FIG. 5 and other flow charts presented herein.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data from external device 40 via a radio frequency (RF) communication link as described above. Pacemaker 100 may receive pacing and sensing control parameters via telemetry module 208 and store the control parameter values in memory 210 for access by control module 206. ATP therapy parameters, such as ATP type (e.g., burst, ramp, ramp plus burst, etc.), number of pulses, number of ATP sequences, etc., may be received by telemetry module 208 from external device 40. ATP therapy control parameters may be selected to terminate monomorphic VT with a high degree of likelihood within a predetermined time limit or expected time of ICD capacitor charging leading up to shock delivery by ICD 14 if needed.

Pacemaker 100 may transmit data, such as EGM signal data, and in particular EGMs signal data associated with detected VT episodes, to external device 40. Transmitted data may be reviewed by a clinician or technician for use in programming VT detection parameters to improve the sensitivity and specificity of detecting monomorphic VT using the presently disclosed techniques.

In some examples, pacemaker 100 may transmit RF signals to ICD 14 via telemetry module 208 to confirm VT detection and/or ATP delivery. In other examples, pacemaker 100 may signal ICD 14 that VT has been detected and/or that ATP therapy is imminent, being delivered or completed via a TCC protocol that utilizes signals sent via electrodes 162 and 164.

Figure 4:
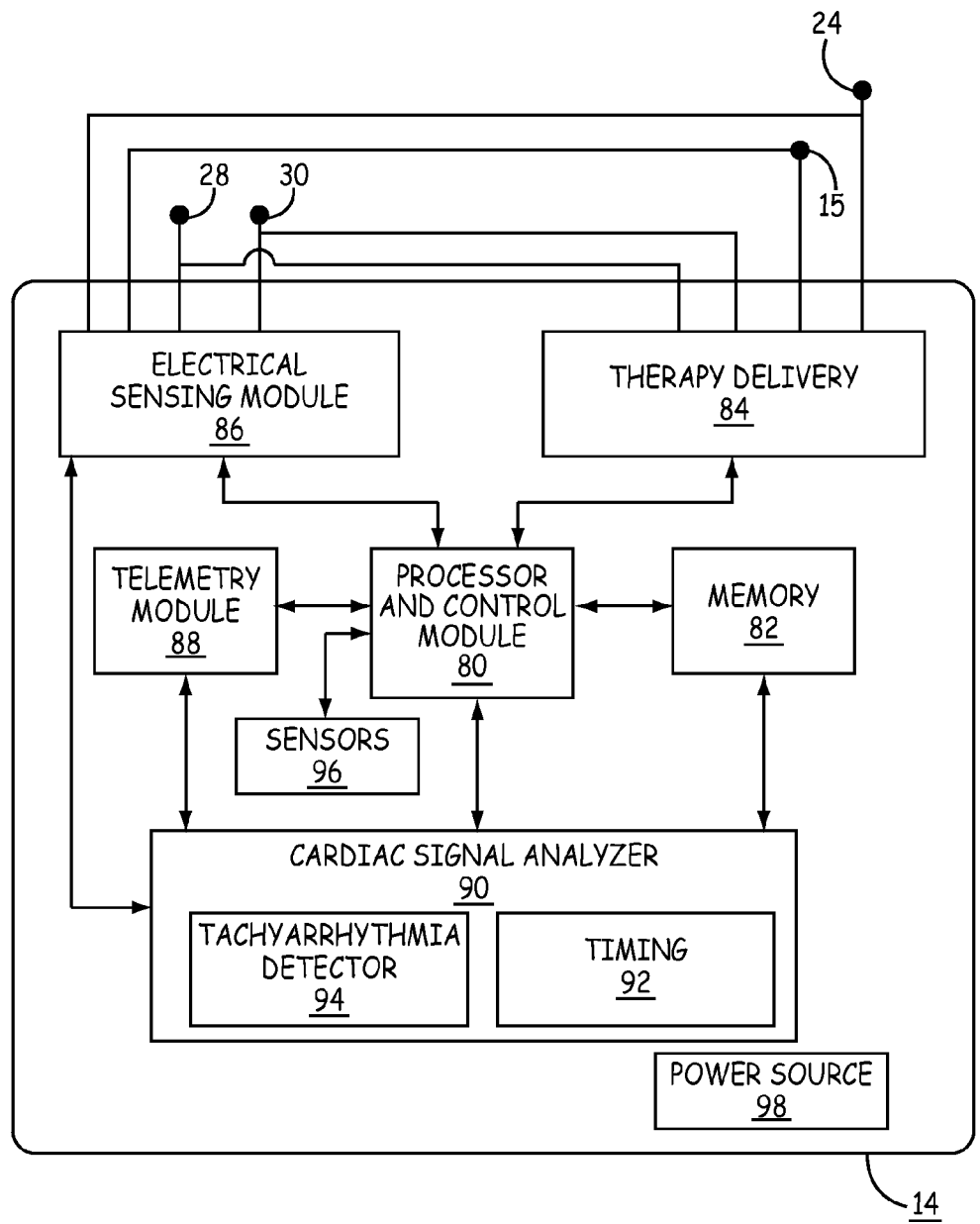
FIG. 4 is a schematic diagram of the ICD shown in FIG. 1A according to one example.

FIG. 4 is a schematic diagram of ICD 14 according to one example. The electronic circuitry enclosed within housing 15 includes software, firmware and hardware that cooperatively monitor one or more ECG signals, determine when a CV/DF shock is necessary, and deliver prescribed CV/DF shock therapies. In some examples, ICD 14 may be coupled to a lead, such as lead 16, carrying electrodes, such as electrodes 24, 28 and 30, positioned in operative relation to the patient's heart for delivering cardiac pacing pulses, e.g., post-shock bradycardia pacing, in addition to shock therapies.

ICD 14 includes processor and control module 80, memory 82, therapy delivery module 84, electrical sensing module 86, telemetry module 88, and cardiac signal analyzer 90. A power source 98 provides power to the circuitry of ICD 14, including each of the modules 80, 82, 84, 86, 88, and 90 as needed. Power source 98 may include one or more energy storage devices, such as one or more rechargeable or non-rechargeable batteries.

The functional blocks shown in FIG. 4 represent functionality that may be included in ICD 14 and may include any discrete and/or integrated electronic circuit components that implement analog and/or digital circuits capable of producing the functions attributed to ICD 14 herein. For example, the modules may include analog circuits, e.g., amplification circuits, filtering circuits, and/or other signal conditioning circuits. The modules may also include digital circuits, e.g., analog-to-digital converters, combinational or sequential logic circuits, integrated circuits, processors, ASICs, memory devices, etc.

Memory 82 may include any volatile, non-volatile, magnetic, or electrical non-transitory computer readable storage media such as those listed previously herein. Furthermore, memory 82 may include non-transitory computer readable media storing instructions that, when executed by one or more processing circuits, cause processor and control module 80 or other ICD modules to perform various functions attributed to ICD 14. The functions attributed to IMD system 10 may be executed by system control circuitry including ICD processor and control module 80 and pacemaker control module 206. The system control circuitry may execute instructions stored by discrete or distributed non-transitory, computer-readable storage media to cause IMD system 10 to perform the functions disclosed herein.

Processor and control module 80 communicates with therapy delivery module 84, cardiac signal analyzer 90 and electrical sensing module 86 for sensing cardiac electrical activity, detecting cardiac rhythms, and generating electrical stimulation therapies in response to sensed signals. Therapy delivery module 84 and electrical sensing module 86 are electrically coupled to electrodes 24, 28, and/or 30 carried by lead 16 (shown in FIG. 1) and housing 15, which may serve as a common or ground electrode.

Electrical sensing module 86 is selectively coupled to sensing electrodes 28, 30 and housing 15 in order to monitor electrical activity of the patient's heart. Electrical sensing module 86 may additionally be selectively coupled to defibrillation electrode 24. Sensing module 86 is enabled to selectively monitor one or more sensing vectors selected from the available electrodes 24, 28, 30 and 15. For example, sensing module 86 may include switching circuitry for selecting which of electrodes 24, 28, 30 and housing 15 are coupled to sense amplifiers included in sensing module 86. Switching circuitry may include a switch array, switch matrix, multiplexer, or any other type of switching device suitable to selectively couple sense amplifiers to selected electrodes.

In some examples, electrical sensing module 86 includes multiple sensing channels for sensing multiple ECG sensing vectors selected from electrodes 24, 28, 30 and housing 15. For example, sensing module 86 may include two sensing channels. Each sensing channel may include a sense amplifier or other cardiac event detection circuitry for sensing cardiac events, e.g., R-waves, from the received ECG signal developed across the selected electrodes 24, 28, 30 or 15. Each time the received ECG signal crosses the auto-adjusting sensing threshold outside a blanking interval, a cardiac event sense signal, such as an R-wave sense event signal, is produced and passed to processor and control module 80 and/or cardiac signal analyzer 90 for use in detecting VT and VF.

Sensing module 86 may include an analog-to-digital converter for providing a digital ECG signal from one or all available sensing channels to processor and control module 80 and/or cardiac signal analyzer 90. For example two ECG signals as described above may each be converted to a multi-bit digital signal by sensing module 86 and provided to tachyarrhythmia detector 94 for performing ECG morphology analysis. Analysis of the ECG signal morphology may be performed by cardiac signal analyzer 90 for detecting VT and VF.

Cardiac signal analyzer 90 includes a tachyarrhythmia detector 94 for detecting VT and VF and discriminating VT and VF from sinus tachycardia and supraventricular tachycardia rhythms as well as identifying different forms of VT such as monomorphic VT and polymorphic VT. Cardiac signal analyzer 90 may further include a timing circuit 92 that includes various timers and/or counters for measuring time intervals, such as RRIs, setting time windows such as morphology template windows, morphology analysis windows or for performing other timing related functions of cardiac signal analyzer 90 including synchronizing cardioversion shocks or other therapies delivered by therapy delivery module 84 with sensed cardiac events.

In some examples, the timing of R-wave sense event signals received from sensing module 86 is used by timing circuit 94 to determine RRIs between sense event signals. Tachyarrhythmia detector 94 may count RR intervals measured by timing circuit 92 that fall into different rate detection zones for determining a ventricular rate or performing other rate- or interval-based assessment for detecting and discriminating VT and VF.

Examples of algorithms that may be performed by ICD 14 for detecting, discriminating and treating rhythms by CV/DF shock, which may be adapted for inclusion in IMD system 10 described herein, are generally disclosed in U.S. Pat. No.

5,354,316 (Keimel); U.S. Pat. No. 5,545,186 (Olson, et al.); U.S. Pat. No. 6,393,316 (Gillberg et al.); U.S. Pat. No. 7,031,771 (Brown, et al.); U.S. Pat. No. 8,160,684 (Ghanem, et al.), and U.S. Pat. No. 8,437,842 (Zhang, et al.), all of which patents are incorporated herein by reference in their entirety. The detection algorithms are highly sensitive and specific for the presence or absence of life threatening VT and VF.

In some examples, ICD tachyarrhythmia detector 94 analyzes n-second cardiac signal segments for detecting VT/VF. For example, based on an analysis of the ECG signal morphology across an n-second segment, which is a 3-second segment in some examples, the segment is classified as "shockable" or "non-shockable." If at least two out of three consecutive n-second segments are classified as shockable, the rhythm is detected as a "shockable rhythm" that is potentially life-threatening and may require a CV/DF shock in order to terminate the VT/VF. Rhythms detected as "shockable" rhythms by ICD 14 may include polymorphic VT and VF and may include monomorphic VT. However, ICD 14 may apply a shock delay time interval in response to monomorphic VT detection in order to allow pacemaker 100 to attempt ATP delivery for terminating the VT before delivering a CV/DF shock.

It should be noted that implemented arrhythmia detection algorithms may utilize not only ECG signal analysis methods but may also utilize supplemental sensors 96, such as blood pressure, tissue oxygenation, respiration, patient activity, heart sounds, and the like, for contributing to a decision by processing and control module 80 to apply or withhold a therapy.

Therapy delivery module 84 includes a high voltage (HV) therapy delivery module including one or more HV output capacitors. When VT/VF rhythm is detected the HV capacitors are charged to a pre-programmed voltage level by a HV charging circuit. Control module 80 applies a signal to trigger discharge of the HV capacitors upon detecting a feedback signal from therapy delivery module 84 that the HV capacitors have reached the voltage required to deliver a programmed shock energy. In this way, control module 80 controls operation of the HV output circuit of therapy delivery module 84 to deliver high energy CV/DF shocks using defibrillation electrode 24 and housing 15. Timing circuit 92 may be used to control R-wave synchronized shock pulses delivered by therapy delivery module 84.

ICD 14, being implanted subcutaneously and therefore relatively larger than intracardiac pacemaker 100, may have greater processing capacity than pacemaker 100. ICD 14 may therefore implement advanced VT/VF detection and discrimination algorithms that detect VT and VF with high sensitivity and specificity using higher level algorithms and discriminators. When a VT/VF detection is made that causes processor and control module 80 to schedule a CV/DF shock, charging of high voltage capacitors included in therapy delivery module 84 can take up to several seconds. When the rhythm is a monomorphic VT, the rhythm may be successfully terminated by ATP, precluding the need for the high energy shock which can be painful to the patient. Accordingly, in IMD system 10, pacemaker 100 may operate to detect monomorphic VT with high sensitivity and specificity to enable ATP delivery during capacitor charging, or at least prior to shock delivery by ICD 14. If the VT is not successfully terminated by the ATP, the ICD 14 confirms the VT detection upon completing capacitor charging and delivers the scheduled shock. If the ATP was successful, the VT is no longer detected by ICD 14 upon completion of capacitor charging (or earlier) and the shock is cancelled.

User-programmable therapy delivery control parameters may be programmed into ICD memory 82 via telemetry module 88. Telemetry module 88 includes a transceiver and antenna for communicating with external device 40 (shown in FIG. 1) using RF communication. Telemetry module 88 may receive downlink telemetry from and send uplink telemetry to external device 40. As discussed above, ICD 14 may be configured to send and receive data to/from pacemaker 100 via telemetry module 88. ICD 14 may additionally or alternatively communicate directly with pacemaker 100 using TCC via electrodes 24, 28, 30 and/or housing 15.

ECG episode data related to the detection of VT and the delivery of a CV/DF shock may be stored in memory 82 and transmitted by telemetry module 88 to external device 40 upon receipt of an interrogation command. Clinician review of episode data facilitates diagnosis and prognosis of the patient's cardiac state and therapy management decisions, including selecting programmable control parameters used for detecting shockable VT rhythms and delivering therapy.

Figure 5:
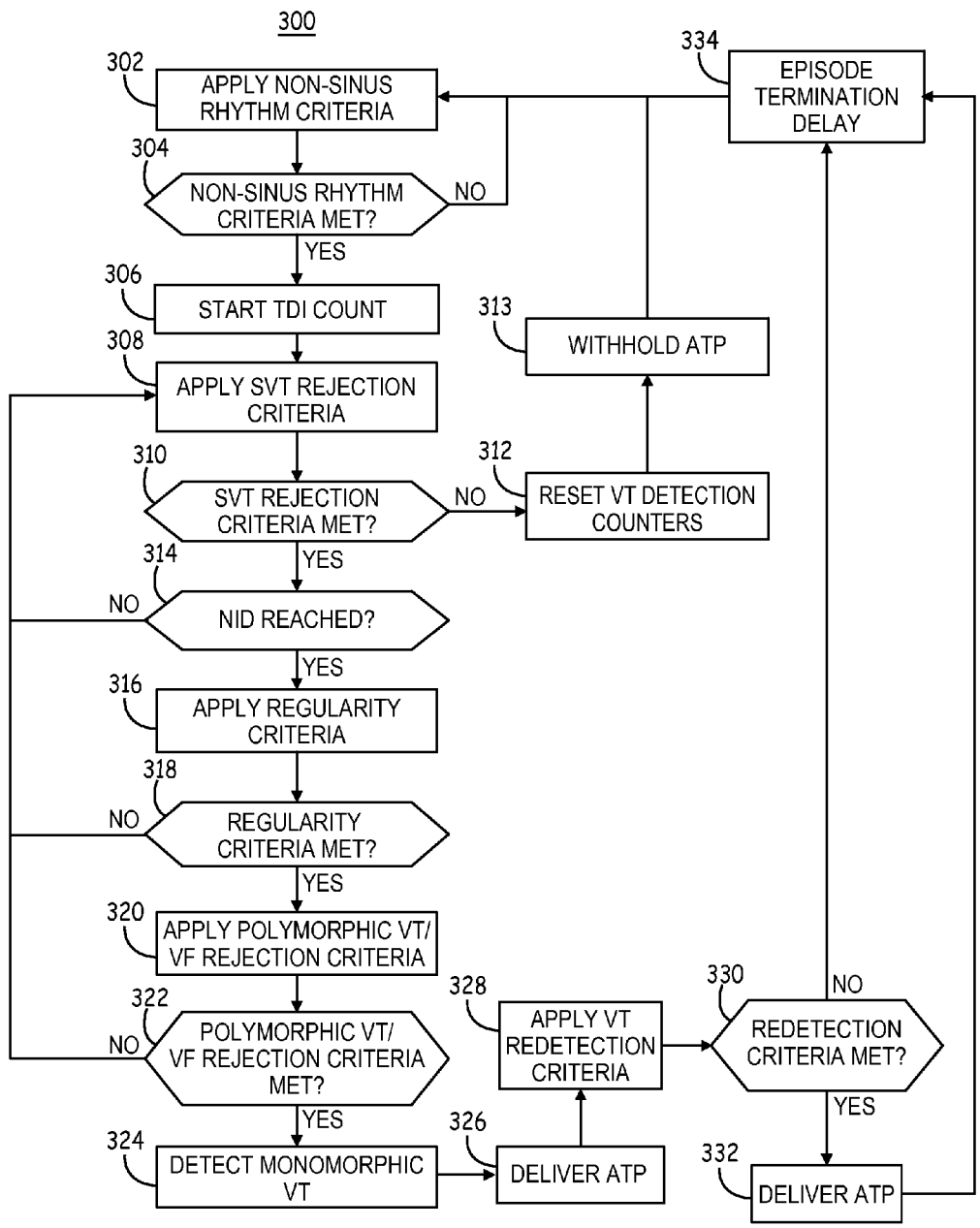
FIG. 5 is a flow chart of a method for detecting monomorphic VT by the pacemaker of FIG. 1A using only RR intervals according to one example.

FIG. 5 is a flow chart 300 of a method for detecting monomorphic VT by pacemaker 100 using only RR intervals according to one example. As described above, pacemaker 100 may be configured to acquire bipolar EGM signals. Atrial P-waves may be very small in amplitude or absent from the bipolar EGM signal acquired in the ventricle. As such, pacemaker 100 may not receive atrial rhythm information in the acquired EGM signal when pacemaker 100 is implanted wholly in a ventricle. Atrial rate information, atrial to ventricular event intervals (PR intervals), and the relationship between atrial and ventricular rates is not available to pacemaker control module 206 for detecting VT and discriminating VT from SVT. Furthermore, pacemaker 100 may be miniaturized for transcatheter intracardiac implantation such that it has a limited power supply and processing capacity compared to subcutaneously implanted devices. Advanced methods for analyzing the QRS waveform, e.g., using wavelet transforms or other morphology matching algorithms, and/or analysis of other higher level rhythm discriminators for detecting and discriminating SVT, monomorphic VT, polymorphic VT and/or VF may be unavailable without compromising the longevity of the pacemaker battery life.

Detection of monomorphic VT with high sensitivity and specificity is desired since ATP delivered in response to false VT detection may adversely accelerate the ventricular rhythm in some patients. ATP during SVT is unlikely to terminate the SVT and is therefore undesirable. Rejection of polymorphic VT/VF with high specificity is desired since polymorphic forms of VT/VF are not expected to respond well to ATP. Delivering ATP during polymorphic VT/VF may delay detection of the abnormal rhythm by ICD 14 since ATP pulses may confound ICD sensing of cardiac signals. Accordingly, pacemaker 100 is configured to detect monomorphic VT with high sensitivity and reject SVT and polymorphic VT/VF with high specificity such that only monomorphic VT is detected with high sensitivity and specificity and is therefore the only tachyarrhythmia detected and treated by pacemaker 100. The monomorphic VT detection techniques implemented in pacemaker 100 use only RR interval (RRI) based criteria which can be applied without high processing burden.

High specificity for rejecting SVT and polymorphic VT/VF may result in some underdetection of monomorphic VT episodes by pacemaker 100 such that ATP is withheld when the VT is potentially treatable by ATP in some instances. Since ICD 14 will detect and treat the VT, however, the rhythm does not go untreated by IMD system 10. The overall system 10 including ICD 14 and pacemaker 100 still provides very high sensitivity to detecting and treating all potentially malignant ventricular rhythms. As such, the techniques of flow chart 300 are implemented in pacemaker 100 to enable monomorphic VT detection with high specificity and sensitivity but with a tendency toward underdetection of a monomorphic VT when there is some probability of the rhythm being an SVT or a polymorphic VT/VF. SVT and polymorphic VT/VF rejection criteria are applied to minimize the likelihood of overdetection of SVT or polymorphic VT/VF as being monomorphic VT and thereby minimize the likelihood of delivering ATP by pacemaker 100 during an SVT or polymorphic VT/VF.

At block 302, non-sinus rhythm criteria are applied to RRIs that are determined between consecutive R-wave sensed event signals received by control module 206 from sensing module 204. Control module 206 does not begin counting tachycardia detection intervals (TDIs), e.g., RRIs falling into a predefined TDI range, to detect VT until non-sinus rhythm criteria are met. When the non-sinus rhythm criteria are met, a non-sinus VT may be evolving. The non-sinus rhythm criteria may include criteria for detecting a rapid increase in ventricular rate, e.g., by detecting a rapid shortening of RRIs. During sinus rhythm, a rapid shortening of RRIs does not normally occur. Detecting a rapid onset of a fast ventricular rate, therefore, provides one way of discriminating between the onset of VT and the onset of sinus tachycardia. The heart rate increases gradually during sinus tachycardia causing shortening of the RRIs that is more gradual than the shortening of RRIs at the onset of a fast, monomorphic VT that may be appropriately treated by ATP. One example of applying non-sinus rhythm criteria to RRIs determined by control module 206 is described in conjunction with FIG. 6 below in which the average RRIs of consecutive groups of RRIs are compared to detect a rapid onset of a non-sinus, fast ventricular rhythm. Control module 206 monitors RRIs at block 302 until the non-sinus rhythm criteria are met at block 304.

Once the non-sinus rhythm criteria are met, control module 206 begins to count TDIs (at block 306). RRIs that occur after the non-sinus rhythm criteria are satisfied and are equal to or shorter than a maximum TDI are counted as TDIs. In some examples, all RRIs less than or equal to the maximum TDI are counted as TDIs. In other examples RRIs that are less than or equal to the maximum TDI and greater than or equal to the minimum TDI are counted as TDIs. The maximum TDI may be programmable and may be, without limitation, 270 ms to 330 ms. A minimum TDI may be programmable and may be set to 220 ms. As such, in one example, after the non-sinus rhythm criteria are met at block 304, each subsequent RRI that is greater than or equal to 220 ms and less than or equal to 330 ms is counted as a TDI. In other instances, the TDI range is set to 200 ms to 300 ms. In various examples, the minimum TDI may be programmably set between and including 180 ms and 240 ms and the maximum TDI may be programmably set between and including 260 ms and 350 ms.

During the TDI counting, control module 206 applies SVT rejection criteria to the RRIs being determined on a beat-by-beat basis at block 308. If SVT rejection criteria become unmet, as determined at block 310, the TDI counter (and any other non-zero VT detection counters) is/are reset to zero at block 312. VT is not detected and ATP is withheld at block 313. The process returns to block 302 to wait for the non-sinus rhythm criteria to be met again before a VT detection can be made in some examples. In other examples, the process may clear the TDI counter at block 312 and return to block 306 to restart TDI counting without requiring the non-sinus rhythm criteria to be met again, i.e., without necessarily returning to block 302. Example techniques performed by control module 206 for counting TDIs and applying SVT rejection criteria are described below in conjunction with FIG. 7.

If the SVT rejection criteria are met at block 310, and the TDI count reaches a required number of intervals to detect (NID) as determined at block 314, the process advances to block 316 to apply RRI regularity criteria. In an illustrative example, in order to advance to block 316, the TDI count must reach N within M consecutive RRIs, e.g., at least 30 (N) out of 40 (M) consecutive RRIs. As long as the SVT rejection criteria continue to be met, the control module 206 will continue to count TDIs until N out of M consecutive RRIs are less than the maximum TDI (or less than the maximum TDI and greater than the minimum TDI). Blocks 306 through 314 may be performed by comparing RRIs to the maximum TDI (or the TDI range) and to SVT rejection criteria on a beat-by-beat basis in some examples, as described in below in conjunction with FIG. 7. In other examples, control module 206 may compare RRIs to the TDI range on a beat-by-beat basis and if the NID is reached apply the SVT rejection criteria to the group of beats meeting the NID before advancing to block 316 for applying regularity criteria.

The NID requirement may be generally higher than the NID requirement that might be used by ICD 14 to initiate capacitor charging in order to promote high specificity of true, sustained VT detections. The N out of M requirement may vary between embodiments and is selected to achieve the desired sensitivity and specificity for detecting monomorphic VT. For example, with no limitation intended, N may range from 20 to 40 TDIs out of M RRIs where M may be in the range of 25 to 50 RRIs. N may be equal to or less than M. The N out of M TDI requirement may also be based on the time that ICD 14 is expected to require to detect the same VT and begin or complete capacitor charging. For example, N may be selected to be approximately the number of RR intervals that occur at a maximum TDI during a VT detection algorithm performed by ICD 14.

To illustrate, if ICD 14 requires that at least two out of three 3-second ECG signal segments are classified as shockable to start capacitor charging, the number of 320 ms RRIs during two 3-second segments is approximately 19. As such, in one example, a count of at least 20 TDIs may be required to satisfy the NID at block 314 so that by the time VT is detected by pacemaker 100, ICD 14 has already detected the VT and is starting ICD capacitor charging for shock delivery. Pacemaker 100 can then deliver ATP therapy during ICD capacitor charging in preparation for delivering a shock if the pacemaker-delivered ATP does not terminate the VT. Additional examples of establishing a threshold number of TDIs required to detect VT based on an expected time for ICD 14 to detect the same VT episode and begin or complete capacitor charging are described below in conjunction with FIG. 10.

If the NID criteria are satisfied at block 314, regularity criteria are applied at block 316 to RRIs determined by control module 206 leading up to the NID being reached. Fast RRIs during atrial fibrillation tend toward greater RRI variation than monomorphic VT. As such, control module 206 verifies that RRIs determined after the non-sinus rhythm criteria are met at block 305 also meet RRI regularity criteria at block 318. An example method for applying regularity criteria to the RRIs determined by control module 206 is described below in conjunction with FIG. 8.

If the regularity criteria are met, criteria rejecting polymorphic VT/VF are applied at block 320. RRIs occurring during TDI counting that are very short, e.g., less than a minimum TDI, may indicate that the rhythm has some probability of being polymorphic VT/VF. Techniques for applying polymorphic VT/VF rejection criteria based on RRIs are described below in conjunction with FIG. 9. ATP may not have a high success rate in treating polymorphic VT and shock delivery may be more urgent if the patient is unstable. As such, additional criteria may be applied to confirm that the VT detected based on a threshold number of TDIs being reached, and other RRI-based criteria described above, is a monomorphic VT that is likely to be responsive to ATP therapy.

If the regularity criteria are not satisfied or the polymorphic VT/VF rejection criteria are not satisfied, a VT detection is not made by control module 206 despite the NID being satisfied after the non-sinus rhythm criteria are met. Control module 206 may return to block 308 to apply SVT rejection criteria and continue to update the TDI counter on a beat-by-beat basis until the regularity criteria and polymorphic VT/VF rejection criteria are satisfied or until the SVT rejection criteria become unmet at block 310. In other words, as long as the SVT rejection criteria continue to be met at block 308 and the NID continues to be met at block 314, monomorphic VT may still be detected if the regularity criteria and the polymorphic VT/VF rejection criteria eventually become satisfied.

In other examples, control module 206 may reset the VT detection counters and return to block 306 to re-start counting TDIs if the regularity and/or polymorphic VT/VF rejection criteria are not satisfied. Control module 206 may restart counting TDIs without requiring the non-sinus rhythm criteria being met again as long as the SVT rejection criteria remain met. In other examples, the non-sinus rhythm criteria may be required to be re-satisfied by returning to block 302 (e.g., via block 312 and/or 313) before a VT detection can be made when the regularity criteria or the polymorphic VT/VF rejection criteria are not satisfied after the NID is reached. In other words, if one or both of the regularity and/or polymorphic VT/VF rejection criteria are not satisfied, pacemaker 100 may reset VT detection counters and/or withhold delivery of ATP therapy.

If the SVT rejection criteria are unmet at block 310 while waiting for the regularity and polymorphic VT/VF rejection criteria to be met, the VT detection counters (e.g., TDI counter, RRI histogram counters, any other VT detection counters used in applying RRI-based VT detection criteria) are reset at block 312. Monomorphic VT is not detected. ATP therapy is withheld at block 313 and is not delivered by pacemaker 100.

If the regularity criteria and the polymorphic VT/VF rejection criteria are both met (blocks 318 and 322 respectively), pacemaker 100 detects monomorphic VT at block 324. Control module 206 controls pulse generator 202 to deliver ATP at block 326 in an attempt to terminate the VT. This process of detecting VT and delivering ATP may occur within a time interval required to detect VT by ICD 14 and to charge the high voltage capacitors for delivering a CV/DF shock by ICD 14.

After delivering a first sequence of ATP at block 326, control module 206 may apply VT redetection criteria at block 328 to redetect the VT if the ATP was unsuccessful. The VT redetection criteria may exclude the non-sinus rhythm criteria applied at block 302 for an initial VT detection and may exclude other VT detection criteria applied to make the initial VT detection, such as the regularity criteria. For example, the VT redetection criteria applied to RRIs at block 328 by control module 206 may require an adjusted NID, where either one or both of the N TDIs out of the M consecutive RRIs are adjusted. For example, up to 18 RRIs may be required to fall in the TDI range out of up to 24 consecutive RRIs occurring after ATP is delivered. In the adjusted NID used for redetection, N may equal M and in one example redetection criteria requires 16 out 16 consecutive RRIs be less than the maximum TDI and greater than the minimum TDI in order to redetect monomorphic VT.

If redetection criteria are met at block 330, which may include a reduced threshold number of TDIs in the adjusted NID, pacemaker 100 redetects the VT and may deliver another ATP sequence at block 332. Pacemaker 100 may be configured to redetect the VT episode a single time and deliver a total of two ATP attempts after which control module 206 returns to block 302 to reapply the non-sinus rhythm criteria before detecting VT and delivering ATP again. If the second ATP therapy attempt at block 332 fails, the VT is not redetected by pacemaker 100. All detection and therapy delivery is performed by ICD 14 for terminating the VT rhythm if the second ATP attempt by pacemaker 100 fails to terminate the VT. Pacemaker 100 may be configured to deliver a limited number of ATP therapy delivery sequences, which may be a single ATP therapy sequence, two sequences, or more. Once the limited number of ATP therapy delivery sequences are attempted, pacemaker 100 ceases to deliver ATP therapy to prevent prolonged delay of shock delivery by ICD 14.

After delivering ATP, whether successful or not, control module 206 may apply an episode termination delay requirement at block 334 before returning to block 302 to apply the non-sinus rhythm criteria for detecting a new monomorphic VT episode. When redetection criteria are not satisfied at block 330, the episode termination delay may be a required time interval, for example 3 seconds or more, or a minimum number of consecutive RRIs that are greater than the maximum TDI. When redetection criteria are satisfied and a second ATP therapy is delivered at block 332, the episode termination delay applied by control module 206 may similarly be a predetermined time interval (during which one or more CV/DF shocks may be delivered by ICD 14) or a minimum number of consecutive RRIs greater than the maximum TDI.

The episode termination delay may be the same or different after a successful ATP therapy ("no" branch of block 330) than after delivering a maximum number of ATP sequences (after block 332). In general, the episode termination delay is applied in part to avoid detecting the same VT episode again while ICD 14 is detecting and delivering shock therapy. The episode termination delay may be implemented to promote detection of only new VT episodes after the maximum number of ATP sequences has been delivered.

In various examples, the RRI-based criteria required to be met in order to detect monomorphic VT by pacemaker 100, initially or upon redetection, may include any combination of the non-sinus rhythm criteria, the NID, the SVT rejection criteria, the regularity criteria, and the polymorphic VT/VF rejection criteria. For example, monomorphic VT may be detected when the NID is reached and the polymorphic VT/VF rejection criteria are met. Criteria may be added or eliminated and the number of RRIs, thresholds and other parameters used for determining whether a given criterion is met may be adjusted in order to achieve a desired sensitivity and specificity of detecting monomorphic VT. In some cases, some criteria are not applied until other criteria are satisfied. In other cases, multiple VT detection criteria may be applied simultaneously as RRIs are determined.

Figure 6:
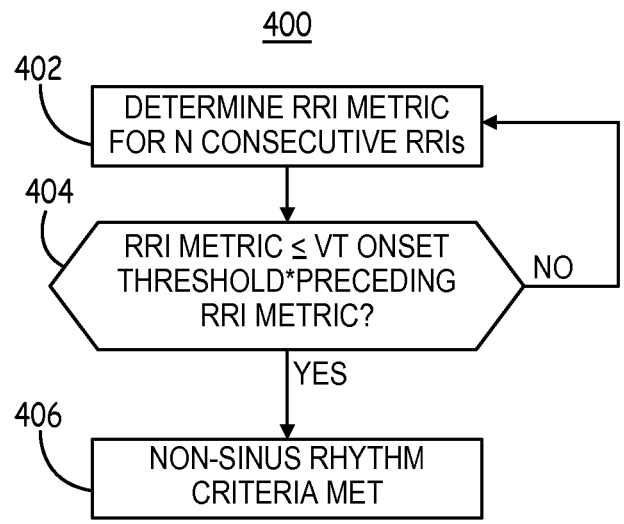
FIG. 6 is a flow chart of a method for applying non-sinus rhythm criteria in the method of FIG. 5 according to one example.

FIG. 6 is a flow chart 400 of a method for applying non-sinus rhythm criteria according to one example and may be used, for example, in blocks 302 and 304 of FIG. 5. At block 402, control module 206 determines an RRI metric for a group of a predetermined number of consecutively determined RRIs. The RRI metric is the average of a group of four consecutive RRIs in one example. In other examples, more or fewer RRIs may be used to determine the RRI metric, e.g., three to eight RRIs may be used. The RRI metric may be, with no limitation intended, an average, median, or mode of the predetermined number of RRIs. The RRI metric is determined for each consecutive, non-overlapping group of the predetermined number of RRIs in one example.

At block 404, the currently determined RRI metric is compared to the most recent preceding RRI metric to determine if non-sinus rhythm criteria are met. A significant decrease in the RRI metric from one group of consecutive RRIs to the next group of consecutive RRIs indicates a rapid onset of a fast VT and is a contraindication of sinus tachycardia or any other sinus rhythm. In one example, the currently determined average RRI for a group of four consecutive RRIs is compared to a VT onset threshold percentage of the preceding average RRI for the preceding group of four consecutive RRIs. Stated differently, the ratio of two RRI averages, one determined from a current group of RRIs and the other determined from the immediately preceding group of RRIs, is compared to the VT onset threshold.

The VT onset threshold may be programmably selected and may be between approximately 70% and 97%. In other examples, the VT onset threshold may be programmably set between 50% and 98%. Before control module 206 begins counting TDIs to determine if a threshold number of TDIs is met, an RRI metric must be less than the VT onset threshold percentage of the immediately preceding RRI metric. A smaller VT onset threshold percentage requires a more rapid acceleration of the RRIs in order to detect VT. In one example, if the average RRI for the most recent four consecutive RRIs is less than 81% of the average RRI for the preceding group of four consecutive RRIs, the non-sinus rhythm criteria are met at block 406.

The process of flow chart 400 may be performed continuously by pacemaker 100 until the non-sinus rhythm criteria are met. To do this, control module 206 may determine and store only the most recent four (or other predetermined number of) RRIs, determine the average of those four RRIs and store that average RRI in memory 210. The average RRI need only be stored until it is compared to the next average RRI at block 404. If that comparison does not meet the non-sinus rhythm criteria, the older RRI metric of the two RRI metrics used for the comparison at block 404 may be overwritten such that only two RRI metrics need to be stored at any given time and only four determined RRIs need to be stored for determining the current RRI metric in the specific example given. As such, continuous monitoring for the non-sinus rhythm criteria being met does not require significant memory or processing time but provides high sensitivity toward the detection of monomorphic VT.

Once the non-sinus rhythm criteria are met at block 406, the control module 206 begins to count TDIs as described in conjunction with FIG. 5 at block 306. The RRI metric determined at block 402 need not be determined again unless SVT rejection criteria become unmet (no branch of block 310 in FIG. 5). The process of flow chart 402 starts again for detecting a new VT episode after SVT rejection criteria become unmet or after monomorphic VT is detected and a limited number of ATP therapy sequences are delivered.

Figure 7:
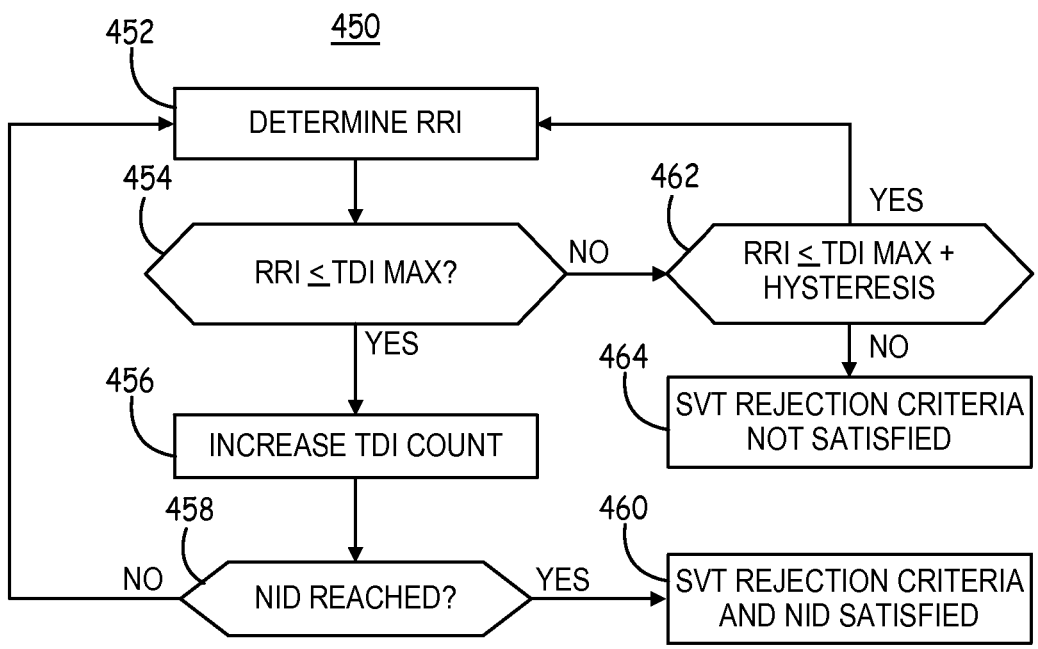
FIG. 7 is a flow chart of a method for applying tachycardia detection interval criteria and supraventricular tachycardia rejection criteria in the method of FIG. 5 according to one example.

FIG. 7 is a flow chart 450 of a method for applying NID and SVT rejection criteria according to one example and may be used, for example, in blocks 306, 308, 310 and 314 of FIG. 5 after non-sinus rhythm criteria are met. Control module 206 begins counting RRIs that fall within a predefined TDI range as described above in conjunction with block 306 of FIG. 5. During TDI counting, before the NID is reached, control module 206 monitors determined RRIs to determine if SVT rejection criteria are met. One example of this process is shown by flow chart 450.

At block 452, control module 206 determines RRIs, e.g., on a beat-by-beat basis, after the non-sinus rhythm criteria are met. At block 454, a determined RRI is compared to the maximum TDI. The maximum TDI may be fixed or programmable and represents the slowest ventricular rate, i.e., longest RRI, considered to be a potentially valid VT beat. The maximum TDI may be programmable up to a value of 330 ms, e.g., between and including 270 ms and 330 ms.

In some examples, the determined RRI is compared to a maximum and a minimum TDI to determine if the RRI falls into a TDI range. The minimum TDI may be fixed or programmable and represents the fastest ventricular rate that is detected by pacemaker 100 as monomorphic VT. Faster rates, i.e., an RRI that is shorter than the minimum TDI, may be VF or a polymorphic VT that is not appropriately treated by ATP. In one example, the minimum TDI is fixed at 220 ms.

If the currently determined RRI is shorter than the maximum TDI at block 454, the TDI counter is increased at block 456 and compared to the NID at block 458. If the determined RRI is not less than the maximum TDI at block 454, it is compared to the maximum TDI plus a hysteresis interval at block 462. The hysteresis interval may be a fixed interval that represents a maximum cycle length jitter that is expected to occur during a true VT. Cycle length jitter (or variation) may cause some RRIs to be longer than the maximum TDI, which are not counted as TDIs even though a VT is in process. If an RRI is even longer than the maximum TDI plus the hysteresis interval, however, the rhythm may be SVT. The hysteresis interval may be a fixed interval stored in memory 210. In one example, the hysteresis interval is fixed at 60 ms but may be programmed to values, with no limitation intended, from 30 ms to 90 ms in one example or from 20 ms to 100 ms in another example.

SVT, such as atrial fibrillation that is conducted to the ventricles, is typically characterized by greater cycle length jitter in the RRIs than monomorphic VT. Some relatively longer RRIs may occur during SVT because some atrial depolarizations during SVT may not be conducted to the ventricles due to refractoriness of the AV node. As such, an RRI longer than the TDI plus the hysteresis interval is evidence of SVT and causes the control module to exit the VT detection process of counting TDIs. As long as all RRIs are less than or equal to the maximum TDI plus the hysteresis interval, the control module 206 continues to count TDIs until the threshold number of TDIs is reached (e.g., the NID is reached). SVT is rejected as a cause of the TDIs as long as all RRIs during TDI counting are less than the maximum TDI plus the hysteresis interval. If the NID is reached during TDI counting, as determined at block 458, control module 206 determines that the SVT rejection criteria have been met along with the NID at block 460. This determination may correspond to the "yes" branch of block 314 (FIG. 5) where control module 206 advances to block 318 to apply the next RRI-based VT detection criteria, e.g., RRI regularity criteria.

If an RRI occurs that is greater than the maximum TDI plus the hysteresis interval at block 462, the SVT rejection criteria are not satisfied at block 464. Block 464 may correspond to the no branch of block 310 of FIG. 5. VT is not detected; the TDI counter is reset at block 312, and ATP is not delivered as indicated at block 313. The process returns to block 302 to begin applying the non-sinus rhythm criteria again. In the example shown, the SVT rejection criteria are unmet, and a VT detection is not made if a single RRI is greater than the maximum TDI plus the hysteresis interval before all other VT detection criteria are satisfied. In other examples, more than one RRI greater than the maximum TDI plus the hysteresis interval may be required before exiting the TDI counting operation and returning to block 302 to apply the non-sinus rhythm criteria. In still other examples, the average of a group of RRIs, e.g., a group of two to five RRIs, may be required to be greater than the maximum TDI plus the hysteresis interval.

Using the hysteresis interval to detect an RRI that is greater than an expected jitter in cycle length during monomorphic VT could cause some underdetection of a true monomorphic VT. In particular, underdetection of a true monomorphic VT episode may occur when only a single RRI greater than the maximum TDI plus the hysteresis interval is required to effectively reject the onset of the fast onset VT detected using the method of FIG. 6. Underdetection of monomorphic VT by pacemaker 100 may be preferred over a falsely detecting SVT as a monomorphic VT, however, since ATP-induced acceleration of the ventricular rhythm is undesired and ICD 14 is present for terminating an underdetected VT with a CV/DF shock if necessary. The hysteresis value may be adjusted to achieve the desired sensitivity and specificity for monomorphic VT detection.

Figure 8:
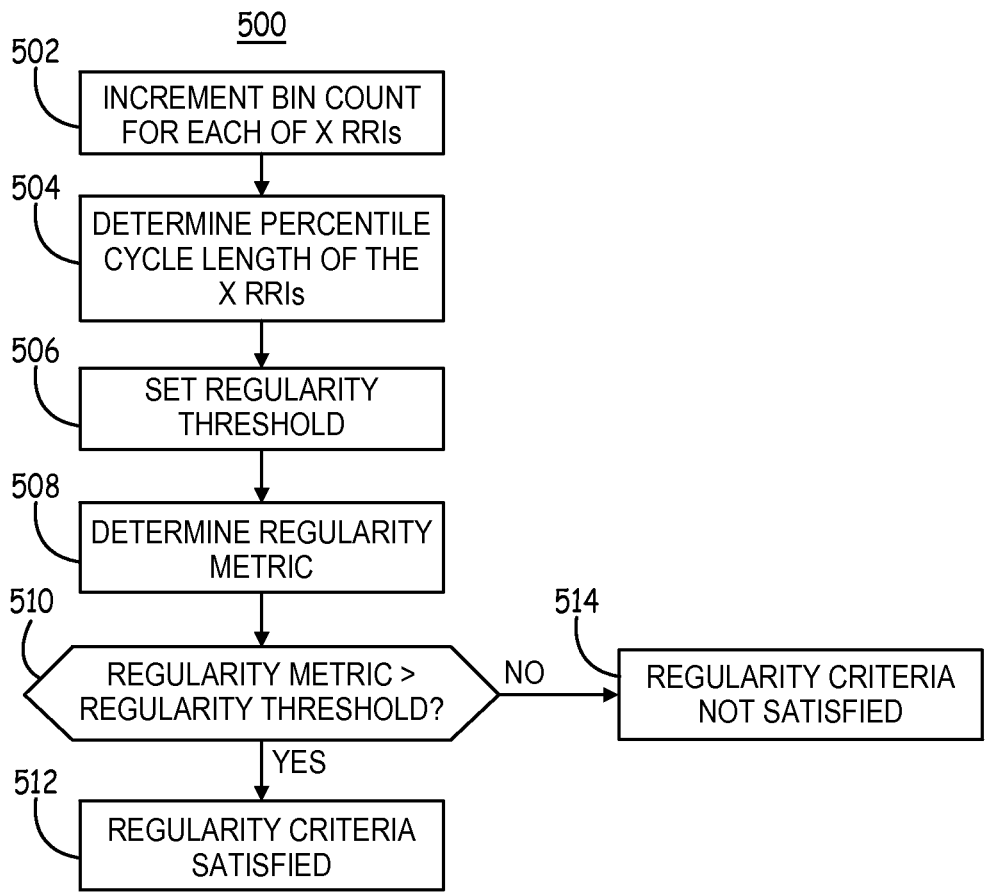
FIG. 8 is a flow chart of a method for applying regularity criteria in the method of FIG. 5 according to one example.

FIG. 8 is a flow chart 500 of a method for applying regularity criteria according to one example and may be used, for example, at blocks 316 and 318 of FIG. 5 when NID criteria and SVT rejection criteria are met. The regularity criteria are applied to RRIs determined after the non-sinus rhythm criteria are met to confirm that the RRIs that led up to the NID criteria being met are TDIs that occur at regular cycle lengths that typify a monomorphic VT. The regularity criteria eliminate polymorphic VT or VF rhythms associated with irregular RRIs. Polymorphic VT/VF rhythms are not intended to be detected by pacemaker 100 for the purposes of triggering delivery of ATP therapy. The regularity criteria may also eliminate some SVT rhythms that cause RRIs to meet the NID criteria but are typically more irregular than monomorphic VT, e.g., due to irregular conduction times through the AV node during atrial fibrillation.

In some examples, the regularity criteria that are applied at block 316 involve counting the determined RRIs that occur in each one of multiple RRI ranges. If the RRI counts are concentrated in a few of the RRI ranges, indicating a high degree of RRI regularity, a monomorphic VT is indicated. If the RRI counts are spread more widely across multiple RRI ranges, the rhythm is unlikely to be a monomorphic VT. Method 500 illustrates one method for implementing RRI regularity criteria.

At block 502, a bin count in an RRI histogram is incremented for each RRI determined after the non-sinus rhythm criteria are satisfied. The histogram total count capacity, X, may be set to all or a portion of the threshold number of TDIs required to detect VT, e.g., equal to N or a fraction thereof. To illustrate, the histogram total count capacity may be set at 18, i.e., 18 RRIs are used to populate the histogram. The histogram is divided into equal RRI (or cycle length) ranges to define multiple cycle length bins. For example, twelve histogram bins may be defined each having a bin width of 16 ms to span a range of cycle lengths (or RRIs) from 120 ms to 432 ms, which encompasses a TDI range which may be set from 200 ms to 320 ms. In other examples, 10 ms bin widths may be used to span all possible RRIs detected between and including a minimum RRI (e.g., 120 ms) to a maximum RRI (e.g., 1500 ms).

In some cases, a monomorphic VT may be characterized by irregular RRIs at its onset which become regular as the VT progresses. As such, RRIs early after the non-sinus rhythm criteria are met (at block 304 of FIG. 5) may be excluded from the RRI analysis for determining if regularity criteria are met in flow chart 500. As such, the total count capacity X of all histogram bins combined may be less than N or M of the NID criteria such that the histogram bin is populated by the X most recent RRIs ending with the RRI that resulted in the NID being reached. Early TDIs counted in the N out of M RRIs toward the NID being reached are excluded from the RRI histogram. For example, if the NID criteria requires that at least 30 TDIs are counted within the most recent 40 RRIs, the RRI histogram total count capacity may be set to 20 or less, such that only the most recent 50% of the RRIs leading up to the NID being satisfied are used for determining RRI regularity. Any irregularity at the onset of the VT episode is ignored.

Bins corresponding to RRIs greater than the maximum TDI plus the hysteresis interval may be excluded in some examples since a single RRI greater than the maximum TDI plus the hysteresis interval may cause the SVT rejection criteria to become unmet, precluding the need to apply the regularity criteria. In still other examples, a single bin counter may be used to count all RRIs of the total count capacity X that are greater than the maximum TDI plus the hysteresis interval. The SVT rejection criteria may become unmet when at least two or more RRIs (or average thereof) are greater than the maximum TDI plus the hysteresis interval. In these cases, the situation may arise when one or more of the X RRIs filling the RRI histogram are greater than the maximum TDI plus the hysteresis interval but did not cause the SVT rejection criteria to become unmet.

Control module 206 increases one histogram bin counter at block 502 for each RRI determined based on which cycle length bin the currently determined RRI falls into. Once the histogram has reached the total count capacity X, e.g., 18, the oldest RRI value is removed from the histogram by decreasing the bin count that was increased by the oldest RRI and the next newest RRI causes a corresponding bin count to be increased.

The control module 206 may wait for the N-X RRIs after the non-sinus rhythm criteria are met to begin populating the RRI histogram, where N is the threshold number of TDIs required to detect VT (and therefore the minimum number of RRIs required for NID to be reached) and X is the histogram total count capacity. In this way, the RRI histogram will be filled to the total count capacity by the time the minimum possible number of RRIs that are required to reach NID have occurred after the non-sinus rhythm criteria are met. To illustrate, if X is 18 and the threshold number of TDIs is 30 out of 40 consecutive RRIs, control module 206 may wait 12 RRIs after the non-sinus rhythm criteria are met and begin increasing the histogram bin counters on the 13th RRI after the non-sinus rhythm criteria are met so that, by the $30^{th}$ RRI, the regularity histogram has reached its total count capacity of 18 RRIs. If the NID is satisfied on the $30^{th}$ RRI, the regularity criteria may be applied immediately to the histogram bin counts.

In other examples, if the total count capacity X equals N of the NID criteria, control module 206 begins populating the histogram by incrementing a histogram bin count starting with the first RRI after the non-sinus rhythm criteria. In still other examples, control module 206 may begin incrementing bin counters starting with the first RRI after the non-sinus rhythm criteria are met regardless of the total count capacity X and adjust count values beat-by-beat as needed after the total count capacity is reached.

After filling the histogram to the total count capacity X, a predetermined percentile cycle length of the X RRIs is determined at block 504. For example, the $75^{th}$ percentile cycle length of the X RRIs populating the histogram may be determined at block 504 (seventy-five percent of the X RRIs are less than the $75^{th}$ percentile cycle length).

This percentile cycle length is used to establish a regularity threshold at block 506. A regularity metric is determined from the RRIs populating the histogram bins at block 508. The regularity metric is compared to the regularity threshold at block 510 to determine if the regularity criteria have been met, as further explained below.

The regularity threshold set at block 506 is the number of RRIs expected to populate the Y largest bin counts corresponding to RRI ranges that are less than the maximum TDI during a monomorphic VT rhythm. In one example, the regularity threshold may be a set at block 506 as a percentage of the total count capacity X, for example 75% of X. The regularity metric determined at block 510, may be the sum of the Y largest bin counts. This regularity metric, or "modesum," is expected to be greater than the regularity threshold established at block 506 if the rhythm is a true monomorphic VT in which RRIs have become regular after the initial VT onset. The use of the modesum as a metric for determining RRI regularity may be implemented according to methods generally disclosed in U.S. Pat. No. 6,879,856 (Stadler, et. al), incorporated herein by reference in its entirety.

In the example given above, if the histogram total count capacity X is 18, the regularity threshold is 14 RRIs. At least fourteen RRIs must populate the Y bins having the largest bin counts in order to detect VT. If Y is selected to be four, the sum of the four largest bin counts out of all the histogram bin counts must be equal to or greater than 14 at block 510 in order to satisfy regularity criteria at block 512. In other examples at least two of the highest bin counts are summed to determine a regularity metric at block 508 that is compared to the regularity threshold at block 510. The number Y of highest bin counts that are summed to determine the regularity metric may depend on the bin widths defined for the RRI histogram. In these examples, the regularity threshold may be set at block 506 to a fixed percentage of the total count capacity X.

In another example, the regularity threshold set at block 508 may depend on what the predetermined percentile cycle length of the X RRIs is at block 506. The regularity threshold is the number of RRIs out of the X RRIs populating the histogram that are expected to fall within the Y largest bin counts when the rhythm is a true monomorphic VT. This expected number may change depending on what the percentile cycle length of the X RRIs is determined to be at block 504. As the percentile cycle length decreases, the number of RRIs expected to occur in the Y highest bin counts may increase. This is because a relatively shorter percentile cycle length, e.g., a relatively short $75^{th}$ percentile cycle length, indicates a relatively higher probability of polymorphic VT or VF. In order to avoid falsely detecting polymorphic VT/VF as a fast monomorphic VT, a higher degree of regularity may be required when the $75^{th}$ percentile cycle length is relatively short. When the $75^{th}$ percentile cycle length is relatively longer, a lesser degree of regularity is required to confirm monomorphic VT since the longer $75^{th}$ percentile cycle length is more likely to be monomorphic VT than polymorphic VT or VF.

In one example, if the percentile cycle length of the X RRIs is relatively short, e.g., less than 270 ms, the regularity threshold established at block 506 is set to 75% of X, e.g., 14 when X is 18. If the percentile cycle length of the X RRIs is greater than or equal to 270 ms but less 400 ms, the regularity threshold may be set to a lower percentage of the total count capacity, e.g., between 40% and 60% of the total count capacity X. If the percentile cycle length is equal to or greater than 400 ms, the regularity threshold is set to an even lower percentage of the total count capacity X, e.g., 28% of X, or 5 when X is 18.

In some examples, the regularity threshold may be set based on a linear function of the percentile cycle length. For instance, the regularity threshold may be determined by control module 206 at block 506 as $(0.75-(CL75-270)/280)*X$, where CL75 is the $75^{th}$ percentile RRI of the X RRIs. Upper and lower bounds may be defined for the regularity threshold. For instance, the regularity threshold may be set according to the linear function of the percentile cycle length up to a maximum of 75% of X and down to a minimum of 25% of X.

The regularity metric determined at block 508 may be referred to as the "modesum" since it is a sum of the bin counts of the Y most frequently occurring RRI ranges less than the maximum TDI in some examples. Other regularity metrics may be determined that reflect the frequency of RRIs occurring within one or more bins (less than the maximum TDI) having the highest bin count(s). When one or more bins are used to count RRIs that are greater than the maximum TDI plus the hysteresis interval, these bins are not selected as any of the Y most frequently occurring RRI ranges because they do not represent TDIs and are therefore not representative of the regularity of TDIs during monomorphic VT.

If the regularity metric, or modesum determined by summing the counts of a predetermined number of the highest bins counts, is not greater than the regularity threshold at block 510, the regularity criteria are not satisfied at block 514. Monomorphic VT is not detected. This result corresponds to the "no" branch of block 318 in FIG. 5. Unless the NID becomes unmet and/or the SVT rejection criteria become unmet, the regularity criteria may continue to be applied on a beat-by-beat basis until satisfied. As new RRIs are determined, they replace the oldest RRIs populating the RRI histogram. As long as NID and SVT rejection criteria remain met, the regularity criteria that were unsatisfied initially may become satisfied. In other examples, the control module 206 may reset VT detection counters to zero, e.g., the TDI counter and the histogram bin counts, if the regularity criteria are not satisfied at block 514 and return to block 306 to re-start TDI counting.

Figure 9:
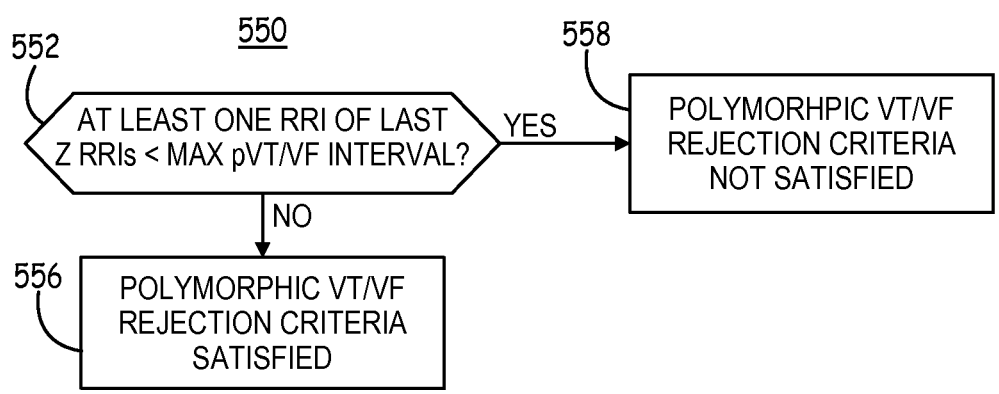
FIG. 9 is a flow chart of a method for applying polymorphic VT and ventricular fibrillation (VF) rejection criteria in the method of FIG. 5 according to one example.

FIG. 9 is a flow chart 550 of a method for applying polymorphic VT/VF rejection criteria according to one example and may be used, for example, at blocks 320 and 322 of FIG. 5. If the NID is reached at block 314 of FIG. 5, polymorphic VT/VF rejection criteria may be applied at block 552 by comparing the most recent Z RRIs preceding the RRI upon which the NID requirement is satisfied to a maximum polymorphic VT/VF threshold. The maximum polymorphic VT/VF threshold may be equal to the minimum TDI, but may be greater than or less than the minimum TDI in other examples. For instance, if at least one RRI that is less than the minimum TDI occurs within the last 8 RRIs (ending with the RRI upon which NID is met), the VT may be a polymorphic VT or VF. Polymorphic VT/VF rejection criteria are not satisfied at block 558.

In other examples, more than one RRI less than maximum polymorphic VT/VF rejection interval may be required to cause the polymorphic VT/VF rejection criteria to be not satisfied. Z in the comparison at block 552 may be any value up to M where M is the M consecutive RRIs used in the N out of M NID criteria. When the maximum polymorphic VT/VF interval is set equal to the minimum TDI and the minimum TDI is used during TDI counting to determine if the NID is reached, Z in block 552 may equal M. In this way, pacemaker 100 may check if any of the M consecutive RRIs that led to the NID being reached were less than the minimum TDI (but weren't counted as a TDI due to being less than the minimum TDI). In this case, more than one of the most recent Z RRIs may be required to be less than the maximum polymorphic VT/VF interval in order for the rejection criteria to be not satisfied at block 558.

If TDIs are counted using only the maximum TDI for determining if the NID is reached, i.e., all RRIs less than or equal to the maximum TDI are counted as TDIs, some of the counted TDIs may also be less than the maximum polymorphic VT/VF interval. In this case, Z may be less than M and may be less than N such that only a most recent portion of the consecutive M RRIs used to reach the NID are used in the comparison at block 552.

If the comparison at block 552 is true, the polymorphic VT/VF rejection criteria are not satisfied at block 558. This result corresponds to the "no" branch of block 322 of FIG. 5. Control module 206 may continue applying the NID criteria, the SVT rejection criteria, the regularity criteria and the polymorphic VT/VF rejection criteria on a beat-by-beat basis until all VT detection criteria are satisfied or until the SVT rejection criteria become unmet. If the SVT rejection criteria become unmet, control module 206 may reset the VT detection counters at block 312 and withhold ATP at block 313 (as shown in FIG. 5).

If all (or another required number) of the most recent Z RRIs ending on the RRI that resulted in the NID being satisfied are greater than or equal to the maximum polymorphic VT/VF interval, as determined at block 552, the polymorphic VT/VF rejection criteria are satisfied at block 556. This result corresponds to the "yes" branch of block 322 of FIG. 5. Pacemaker 100 detects monomorphic VT at block 324 and delivers ATP at block 326. As indicated above, this process of arriving at the monomorphic VT detection at block 324 and delivering ATP by pacemaker 100 occurs within the time required for ICD 14 to detect the VT and charge high voltage capacitors for delivering a shock therapy.

Figure 10:
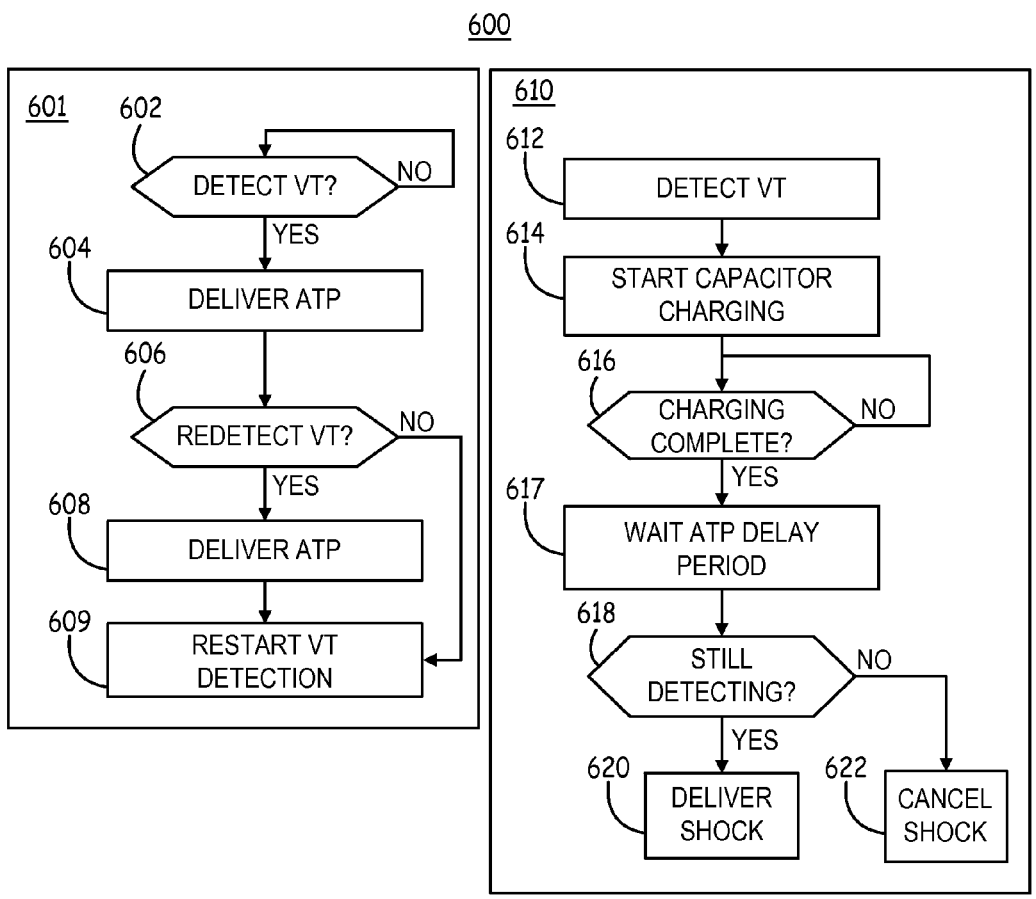
FIG. 10 is a flow chart of a method performed by the IMD system of FIG. 1A for treating VT.

FIG. 10 is a flow chart 600 of a method performed by IMD system 10 for treating VT. The process shown within block 601 is performed by pacemaker 100 and the process shown within block 610 is performed by ICD 14. In some cases, pacemaker 100 and ICD 14 have no direct communication with each other. As such the processes 601 and 610 are performed independently by pacemaker 100 and ICD 14 but are performed concurrently in a coordinated manner for providing safe and effective treatment for terminating fast VTs that may be treatable by ATP.

When pacemaker 100 arrives at a monomorphic VT detection at block 602 according to the RRI-based methods described above in conjunction with FIGS. 5 through 9, ATP is delivered at block 604. In some examples, a single ATP sequence is delivered. Control module 206 returns to block 302 of FIG. 5, in some cases after applying an episode termination delay at block 334, to reapply the non-sinus rhythm criteria before detecting VT again and delivering another ATP sequence. If the monomorphic VT is sustained, it will not be redetected since the rhythm is not meeting the VT onset criteria as described in conjunction with FIG. 6. As a result, ICD 14 will operate to detect and treat the sustained VT.

In other examples, as described above and illustrated in FIG. 10, pacemaker 100 may be configured to redetect the VT at block 606 after delivering ATP using redetection criteria that excludes the non-sinus rhythm criteria and may include an adjusted NID and/or other redetection criteria. Pacemaker 100 may deliver a second ATP sequence at block 608 if the VT is redetected. As such, one or more sequences of ramp, burst, ramp plus burst or other ATP pulse sequences may be delivered by pacemaker 100. In one example, maximum of two sequences of ATP pulses, which may each include 6 to 12 pacing pulses without limitation, are delivered by pacemaker 100 (separated by verifying that VT redetection criteria are met at block 606).

After delivering the second ATP sequence at block 608 (or other predetermined maximum number of ATP sequences), the pacemaker 100 does not attempt to redetect the same VT episode for determining if another ATP sequence should be delivered. Rather, pacemaker 100 ceases therapy delivery allowing ICD 14 to deliver therapy if the VT is sustained or has accelerated after the pacemaker-delivered ATP. At block 609, pacemaker 100 restarts VT detection by monitoring RRIs for satisfying the non-sinus rhythm criteria (block 302 of FIG. 5). As described above in conjunction with block 334 of FIG. 5, an episode termination delay may be applied before pacemaker 100 re-starts VT detection at block 609. The episode termination delay may be implemented by applying episode termination criteria to RRIs determined after the last delivered ATP sequence to verify that normal sinus rhythm has been restored before applying VT detection criteria again. Episode termination criteria may include requiring a threshold number of consecutive RRIs greater than the maximum TDI.

Meanwhile, ICD 14 performs the process 610 beginning at block 612 when ICD 14 detects the VT episode detected by pacemaker 100. ICD 14 may use a different algorithm for detecting VT and VF with both a high specificity and high sensitivity. For example, ICD 14 may use individual QRS waveform morphology, gross ECG morphology, n-second ECG signal segment analysis, or other higher level analyses in addition to RRIs or other criteria for detecting VT and VF. The VT detection made at block 612 may occur earlier, later or at substantially the same time as the VT detection made by pacemaker 100 at block 602.

Upon detecting VT at block 612, ICD 14 begins capacitor charging at block 614. When charging is complete, as determined at block 616 based on a charge complete signal from therapy delivery module 84 to processor and control module 80 (FIG. 4), processor and control module 80 determines if the VT is still being detected at block 618. If so, the scheduled CV/DF shock is delivered at block 620. If the VT is not still being detected, e.g., if the ATP delivered by pacemaker 100 is successful, the shock is canceled at block 622. The high voltage capacitor charge may be discharged through a non-therapeutic load.

The process of detecting VT at block 602 and delivering ATP at block 604 by pacemaker 100 is completed prior to ICD 14 delivering the shock at block 620. In some examples, ICD 14 may be configured to wait for an ATP delay period at block 617 when the VT detected at block 612 is identified as a monomorphic VT that is expected to be detected and treated by pacemaker 100. In other examples, ICD 14 may be configured to detect pacing pulses delivered by pacemaker 100. In this case, ICD 14 may wait until detected pacing pulses corresponding to ATP are no longer being detected, confirm that the VT is still being detected, and deliver the shock at block 620. In other examples, the ICD 14 may be programmed to delay the start of capacitor charging at block 614 when the VT detection is expected to be detected by pacemaker 100 and result in pacemaker-delivered ATP so that capacitor charging is not performed unless necessary.

In order for pacemaker 100 to complete the process of detecting VT (block 602), delivering ATP (block 604), redetecting VT (block 606) and delivering a second ATP sequence (block 608) prior to shock delivery, the threshold number of TDIs required to detect VT after the non-sinus rhythm criteria are satisfied may be selected to ensure that ATP is completed before an expected time to shock delivery by ICD 14 without significantly delaying the shock therapy delivered at block 620. ATP delivered at block 604 begins before capacitor charging is complete, e.g., which may be prior to starting capacitor charging or during capacitor charging. In an illustrative embodiment, the shortest expected time until capacitor charging begins may be approximately 9 RRIs plus one 3-second ECG signal segment or about 18 RRIs occurring at the maximum TDI of 320 ms. In another example, the time for ICD 14 to detect VT and start capacitor charging is expected to be approximately 12 RRIs plus up to two 3-second ECG signal segments or approximately 30 RRIs occurring at the maximum TDI of 320 ms, slightly less than 10 seconds. As such, a threshold number of TDIs may be between 18 TDIs and 30 TDIs to enable pacemaker 100 to detect VT and deliver ATP prior to ICD capacitor charge completion, within 10 seconds in some instances, without significantly delaying shock delivery by ICD 14 when it is needed. In some examples, when ICD 14 detects a monomorphic VT that is expected to be treated by pacemaker 100, ICD 14 may impose an ATP delay period, either before or after capacitor charging, that allows pacemaker 100 at least 10 seconds and up to 20 seconds to detect the monomorphic VT and deliver a limited number of ATP sequences before a shock is delivered.

Figure 11:
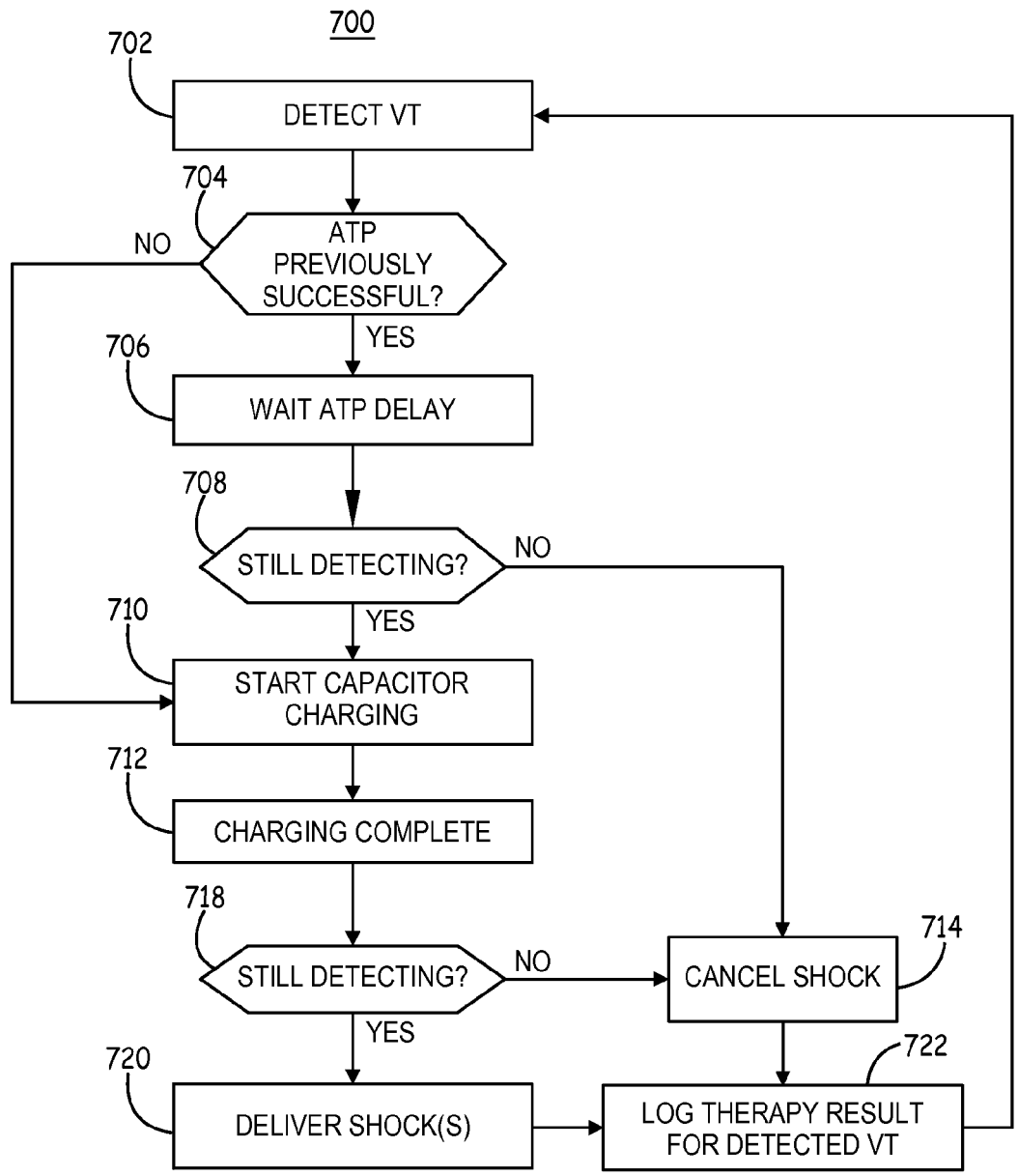
FIG. 11 is a flow chart of a method for controlling capacitor charging by an ICD.

FIG. 11 is a flow chart 700 of a method for controlling capacitor charging by ICD 14 according to one example. At times, ICD 14 may start capacitor charging immediately upon VT detection so that ATP is being delivered during charging to minimize any delay in shock delivery. At other times, it may be acceptable to delay capacitor charging when a high degree of certainty exists that pacemaker-delivered ATP will be successful.

Upon detecting VT at block 702, which may be discriminated as a monomorphic VT depending on the VT detection algorithms implemented in ICD 14, ICD processor and control module 80 determines, at block 704, if the detected VT corresponds to a VT that has been previously detected and successfully terminated by ATP delivered by pacemaker 100. If not, capacitor charging is started immediately at block 710. During charging at block 710, pacemaker 100 is delivering ATP in response to detecting the VT as described above in conjunction with FIG. 10. The process shown by flow chart 700 is performed by ICD 14 and therefore ATP delivery by pacemaker 100 is not shown in FIG. 11, but as described above, is occurring upon monomorphic VT detection by pacemaker 100.

After charging is complete (block 712), ICD 14 confirms whether the VT is still being detected at block 718. If not, the VT has been successfully terminated by the pacemaker 100. The scheduled shock is cancelled at block 714. The therapy result is logged at block 722 for the detected VT.

When the same VT is detected again by ICD 14 at block 702, the previous ATP success logged at block 722 is recognized at block 704. This time, ICD processing and control module 80 may delay capacitor charging by the ATP delay period at block 706. ATP is delivered by pacemaker 100 during the delay period. After the delay period expires, ICD 14 determines if the VT is still being detected, and if so, starts capacitor charging at block 710. Otherwise, the shock is cancelled at block 714 and the successful therapy may be logged again at block 722.

If the VT is still being detected after the ATP delay period at block 708 and after charging is completed at block 718, shock therapy is delivered at block 720. The therapy result is logged at block 722 for the detected VT for use in deciding whether to immediately start capacitor charging or waiting an ATP delay period upon future VT detections. By delaying capacitor charging when a high degree of confidence in successful termination of the VT by pacemaker 100 exists, ICD battery longevity may be increased.

In some examples, the switching from ATP delivery by pacemaker 100 during capacitor charging ("no" branch of block 704) to ATP delivery during an ATP delay period prior to capacitor charging ("yes" branch of block 704) is performed automatically by ICD 14 based on the type of VT detected at block 702 and/or whether or not it has been previously treated by ATP from pacemaker 100. Switching to ATP before capacitor charging occurs only if pacemaker-delivered ATP has been previously successful for a specific VT, e.g., based on the cycle length of the detected VT. Alternatively, a user may program ATP during capacitor charging or ATP before capacitor charging manually along with VT detection parameters based on a review of VT episode detections and therapy results received from ICD 14 and pacemaker 100. When a VT is detected according to programmed detection parameters by ICD 14, capacitor charging is started immediately or after the ATP delay period, according to the programmed selection.

Thus, various embodiments of an implantable medical device system and method have been described for controlling cardiac electrical stimulation therapies in an IMD system including an intracardiac pacemaker and an ICD. However, one of ordinary skill in the art will appreciate that various modifications may be made to the described embodiments without departing from the scope of the following claims.

The invention claimed is:

1. An intracardiac pacemaker comprising:
   a housing sized to fit within a heart;
   at least two electrodes disposed on the housing;
   a sensing module enclosed within the housing and electrically coupled to the at least two electrodes, the sensing module configured to sense R-waves from a first cardiac electrical signal received from the at least two electrodes coupled to the sensing module;
   a pulse generator enclosed within the housing and electrically coupled to the at least two electrodes, the pulse generator configured to generate cardiac pacing pulses for delivery to the heart via the at least two electrodes; and a control module enclosed within the housing and electrically coupled to the sensing module and the pulse generator, the control module configured to:
  determine RR intervals between consecutive ones of the sensed R-waves;
  apply RR interval-based ventricular tachycardia (VT) detection criteria solely to the determined RR intervals;
  detect a monomorphic VT when the VT detection criteria are met; and
  control the pulse generator to deliver anti-tachycardia pacing in response to detecting the monomorphic VT,
  wherein applying the detection criteria solely to the determined RR intervals comprises applying at least a non-sinus rhythm criterion, a supraventricular tachycardia rejection criterion that is different than the non-sinus rhythm criterion, and a number of tachycardia intervals to detect criterion to the RR intervals.

2. The intracardiac pacemaker of claim 1, wherein the control module determines a first average of a first group of the RR intervals, determines a second average of a second group of the RR intervals immediately preceding the first group, compares a ratio of the first average to the second average to a predetermined percentage, and determines that the non-sinus rhythm criterion is met when the ratio of the first average to the second average is less than or equal to the predetermined percentage.

3. The intracardiac pacemaker of claim 1, wherein the control module is configured to apply the non-sinus rhythm criterion, determine that the non-sinus rhythm criteria is met, after determining the non-sinus rhythm criterion is met, determine at least one of the determined RR intervals, compare the at least one of the determined RR intervals that is determined after the non-sinus rhythm criterion is met to a maximum tachycardia detection interval plus a fixed hysteresis interval and determine that the supraventricular tachycardia rejection criterion is not met when the at least one of the determined RR interval that is determined after the non-sinus rhythm criterion is met is greater than or equal to the maximum tachycardia detection interval plus the fixed hysteresis interval.

4. The intracardiac pacemaker of claim 1, wherein the control module is further configured to apply, as part of the detection criteria, a regularity criterion in response to the number of tachycardia intervals to detect criterion being met,
  wherein the regularity criterion is applied to a predetermined number of RR intervals ending with an RR interval that causes the number of tachycardia intervals to detect criterion to be met,
  the predetermined number of RR intervals being less than the number of tachycardia intervals to detect criterion.

5. The intracardiac pacemaker of claim 4, wherein the control module determines a count for each one of a plurality of RR interval ranges by counting RR intervals of the predetermined number of RR intervals that fall into a given one the plurality of RR interval ranges, determine a sum of at least two of the counts having highest values of the determined counts, compare the sum to a regularity threshold, and determine that the regularity criterion is met when the sum is greater than the regularity threshold.

6. The intracardiac pacemaker of claim 5, wherein the control module is further configured to determine a predetermined percentile cycle length of the predetermined number of RR intervals and set the regularity threshold as a function of the predetermined percentile cycle length.

7. The intracardiac pacemaker of claim 1, wherein the control module is further configured to apply, as part of the detection criteria, a polymorphic ventricular tachyarrhythmia rejection criterion in response to the number of tachycardia intervals to detect criterion being met.

8. The intracardiac pacemaker of claim 7, wherein the control module is configured to determine if each one of a predetermined number of the RR intervals ending with an RR interval that causes the number of tachycardia intervals to detect criterion to be met is greater than or equal to a minimum tachycardia detection interval and determine that the polymorphic ventricular tachyarrhythmia rejection criterion is satisfied when all of the predetermined number of RR intervals are greater than or equal to the minimum tachycardia detection interval.

9. The intracardiac pacemaker of claim 8, wherein the control module withholds the delivery of anti-tachycardia pacing therapy in response to the polymorphic ventricular tachyarrhythmia rejection criterion not being satisfied.

10. An implantable medical device system comprising:
  an implantable pacemaker comprising:
    a housing sized to fit within a heart;
    at least two electrodes disposed on the housing;
    a pacemaker sensing module enclosed within the housing and electrically coupled to the at least two electrodes, the pacemaker sensing module configured to obtain R-waves from a first cardiac electrical signal received from the at least two electrodes coupled to the sensing module;
    a pulse generator enclosed within the housing and electrically coupled to the at least two electrodes, the pulse generator configured to generate cardiac pacing pulses for delivery to the heart via the at least two electrodes; and
    a pacemaker control module enclosed within the housing and electrically coupled to the sensing module and the pulse generator, the pacemaker control module configured to:
      determine RR intervals between consecutive ones of the sensed R-waves;
      apply RR interval-based ventricular tachycardia detection criteria solely to the determined RR intervals;
      detect a monomorphic ventricular tachycardia (VT) when the detection criteria are met; and
      control the pulse generator to deliver anti-tachycardia pacing in response to detecting the monomorphic VT,
      wherein applying the detection criteria solely to the determined RR intervals comprises applying at least a non-sinus rhythm criterion, a supraventricular tachycardia rejection criterion that is different than the non-sinus rhythm criterion, and a number of tachycardia intervals to detect criterion to the RR intervals
  an implantable cardioverter defibrillator (ICD) system comprising:
    at least one extravascular defibrillation lead having a plurality of extravascular electrodes;
    an ICD coupled to the at least one extravascular defibrillation lead, the ICD comprising:
      an ICD sensing module electrically coupled to at least a portion of the plurality of extravascular electrodes to receive a second cardiac electrical signal;

a defibrillation therapy delivery module comprising at least one high voltage capacitor, the defibrillation therapy delivery module being configured to deliver a shock therapy to the heart via at least one of the plurality of extravascular electrodes of the extravascular defibrillation lead;

an ICD control module electrically coupled to the ICD sensing module and the defibrillation therapy delivery module, wherein the ICD control module is configured to:

analyze the second cardiac electrical signal received by the ICD sensing module;

detect the monomorphic VT detected by the pacemaker control module in response to the analyzing of the second cardiac electrical signal; and control the therapy delivery module to charge the at least one high voltage capacitor in response to detecting the monomorphic VT, wherein the number of tachycardia intervals to detect criterion comprises requiring a threshold number of the determined RR intervals being less than a tachycardia detection interval, wherein a maximum time interval including the threshold number of the determined RR intervals that are less than the tachycardia detection interval is shorter than an expected time interval required for detecting the monomorphic VT by the ICD and completing charging of the at least one high voltage capacitor by the ICD.

11. The system of claim 10, wherein:

the pacemaker control module is configured to apply the non-sinus rhythm criterion, determine that the non-sinus rhythm criterion is met, determine N predetermined RR intervals, and apply the number of tachycardia intervals to detect criterion by determining whether at least M out of the N predetermined RR intervals that are determined after the non-sinus rhythm criterion is satisfied are less than a maximum tachycardia detection interval, where M and N are predefined values;

the ICD control module is configured to detect the monomorphic VT by analyzing at least one n-second time interval of the second cardiac electrical signal; and M is selected to be at least a maximum possible number of RR intervals that could occur at the maximum tachycardia detection interval in the n-second time interval.

12. The system of claim 10, wherein the ICD control module is further configured to wait for an ATP delay period after detecting the monomorphic VT and before controlling the defibrillation therapy delivery module to charge the high voltage capacitor when a previously detected episode of the monomorphic VT has been successfully terminated by anti-tachycardia pacing delivered by the pacemaker.

13. The system of claim 10, wherein the pacemaker control module determines a first average of a first group of the RR intervals, determines a second average of a second group of the RR intervals immediately preceding the first group, compares a ratio of the first average to the second average to a predetermined percentage, and determines that the non-sinus rhythm criterion is met when the ratio of the first average to the second average is less than or equal to the predetermined percentage.

14. The system of claim 10, wherein the pacemaker control module is configured to apply the non-sinus rhythm criterion, determine that the non-sinus rhythm criteria is met, after determining the non-sinus rhythm criterion is met, determine at least one of the determined RR intervals, compare the at least one of the determined RR intervals that is determined after the non-sinus rhythm criterion is met to a maximum tachycardia detection interval plus a fixed hysteresis interval and determine that the supraventricular tachycardia rejection criterion is not met in response to the at least one RR interval that is determined after the non-sinus rhythm criterion is met is less greater than or equal to the maximum tachycardia detection interval plus the fixed hysteresis interval.

15. The system of claim 10, wherein the pacemaker control module is further configured to apply, as part of the detection criteria, a regularity criterion in response to the number of tachycardia intervals to detect criterion being met, wherein the regularity criterion is applied to a predetermined number of RR intervals ending with an RR interval that causes the number of tachycardia intervals to detect criterion to be met, the predetermined number of RR intervals being less than the number of tachycardia intervals to detect criterion.

16. The system of claim 15, wherein the pacemaker control module determines a count for each one of a plurality of RR interval ranges by counting RR intervals of the predetermined number of RR intervals that fall into a given one the plurality of RR interval ranges, determine a sum of at least two of the counts having highest values of the determined counts, compare the sum to a regularity threshold, and determine that the regularity criterion is met when the sum is greater than the regularity threshold.

17. The system of claim 10, wherein the pacemaker control module is further configured to apply, as part of the detection criteria, a polymorphic ventricular tachyarrhythmia rejection criterion in response to the number of tachycardia intervals to detect criterion being met, wherein the pacemaker control module is configured to determine if each one of a predetermined number of the RR intervals ending with an RR interval that causes the number of tachycardia intervals to detect criterion to be met is greater than or equal to a minimum tachycardia detection interval and determine that the polymorphic ventricular tachyarrhythmia rejection criterion is satisfied when all of the predetermined number of the RR intervals are greater than or equal to the minimum tachycardia detection interval.

* * * * *